United States Patent
Ruegg

(10) Patent No.: US 10,640,537 B2
(45) Date of Patent: May 5, 2020

(54) HOST CELLS AND METHODS USING A REPRESSOR POLYPEPTIDE AND AN INDUCIBLE PROMOTER FOR GENE EXPRESSION

(71) Applicant: The Regents of the University of California, Oakland, CA (US)

(72) Inventor: Thomas L. Ruegg, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/201,248

(22) Filed: Jul. 1, 2016

(65) Prior Publication Data

US 2017/0002363 A1 Jan. 5, 2017

Related U.S. Application Data

(60) Provisional application No. 62/187,767, filed on Jul. 1, 2015.

(51) Int. Cl.
*C07K 14/245* (2006.01)
*C12N 15/63* (2006.01)

(52) U.S. Cl.
CPC ............ *C07K 14/245* (2013.01); *C12N 15/63* (2013.01)

(58) Field of Classification Search
None
See application file for complete search history.

(56) References Cited

U.S. PATENT DOCUMENTS

2014/0038848 A1* 2/2014 Ruegg .................... C12N 15/70
506/10

OTHER PUBLICATIONS

Ruegg et al. 2014 (An auto-inducible mechanism for ionic liquid resistance in microbial biofuel production; Nature Communications; 5: 3490, 1-7) (Year: 2014).*
DeAngelis et al, Complete genome sequence of "Enterobacter lignolyticus" SCF1. Standards in Genomic Sciences (2011) 5:69-85.
Khudyakov et al, Global transcriptome response to ionic liquid by a tropical rain forest soil bacterium, Enterobacter ignolyticus. PNAS (2012) E2173-E2182.
Ogawa et al, KmrA Multidrug Efflux Pump from Klebsiella pneumoniae. Biol. Pharm. Bull. (2006), 29(3) 550-553.
Santiviago et al, The *Salmonella enterica* sv. *Typhimurium* smvA, yddGand ompD (porin) genes are required for the efficient efflux of methyl viologen. Molecular Microbiology (2002) 46(3), 687-698.
Guo et al, Protein tolerance to random amino acid change. PNAS (2004) 101:25, 9205-9210.
Grkovic et al, Interactions of the QacR Multidrug-Binding Protein with Structurally Diverse Ligands: Implications for the Evolution of the Binding Pocket. Biochemistry (2003), 42, 15226-15236.

* cited by examiner

*Primary Examiner* — Mary Maille Lyons
(74) *Attorney, Agent, or Firm* — Robin C. Chiang; Lawrence Berkeley National Laboratory

(57) ABSTRACT

The present invention provides for a system comprising (a) a first nucleic acid comprising a nucleotide sequence encoding a nucleotide sequence of interest operatively linked to a promoter comprising a repressor polypeptide binding site, and (b) a second nucleic acid comprising a nucleotide sequence encoding a repressor polypeptide having at least 70% amino acid identity with EilR, SmvR, KmrR, RcdA, or QacR; wherein expression of the nucleotide sequence of interest from the promoter is induced by the presence of a hydrophobic inducer, such as a hydrophobic cation inducer, such as a triarylmethane, acridine, phenazine, phenothiazine, or xanthene.

18 Claims, 15 Drawing Sheets
Specification includes a Sequence Listing.

- Acridines
  - Acridine Orange
  - Acridine Yellow
  - Proflavine
  - Acriflavine

- Triarylmethanes
  - Crystal violet
  - Malachite green

- Phenazines
  - Neutral red

- Fluorone dyes
  - Rhodamine 6G
  - Rhodamine B

- Imidazoles
  - Ionic liquids

EilR amino acid sequence:
MGYLNREERRETIMQAAMRVALDQGFTGMTVRNIATAAGVAAGQVHHHFTSSGELKSQ
AFIRVIREMMDLQRLSRTAGWREQLFSALGSEDGRLEPYIRLWRQAQLLADSDPEIKSAYL
LTMNLWHDEAVRIIRAGHAAGEFTLRDSAENIAWRLISLVCGLDGIYVLGMPEVDDAAFT
RHLQHVIQLELFS examples of eil-operators:
CAAACTGGACGgaTGTCCAGCTTT (native *E. lignolyticus* eil-operator 1)
AAAGCTGGACAagTGTTCAACTTT (native *E. lignolyticus* eil-operator 2)
AAAGTTGGACAnnTGTCCAACTTT (consensus operator)

Figure 2

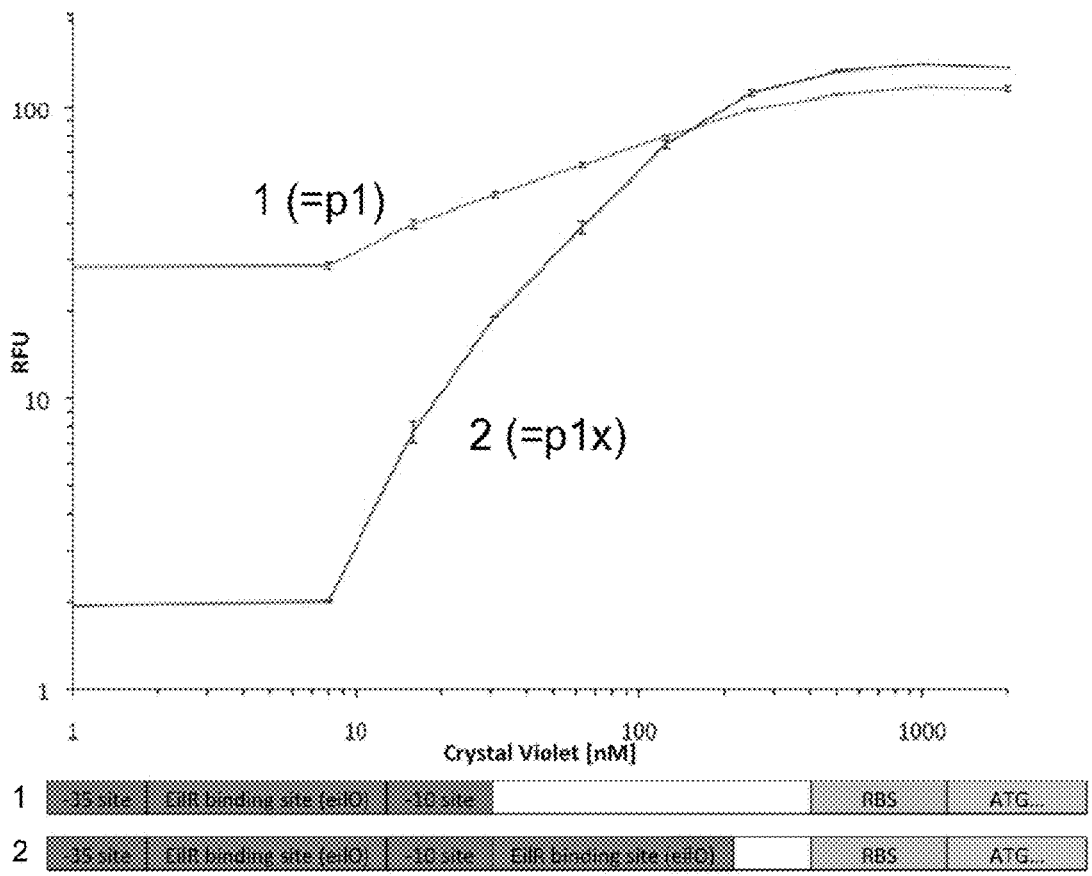

Figure 3

```
BAD AVG GOOD
EilR        : 98
SmvR        : 98
BRL6_KmrR   : 89
QacR        : 71
cons        :  8

EilR        MGVLNPEEFRETIMQAMRVALDQFIQHTVRNIATAAGVAAGVHHHFTSSGELKQDAFIRVIREMMQ
SmvR        MSVLNPDERREVILQAMRVALELFLHITVFNIASEADVAAGVHHHFSSAGELKALAFVHLIRTLLD
BRL6_KmrR   MSVLNDDALREVIVLAMRVALDGLFLHITVHDIAAEAGVAAGVHHHFTSAGELKDHTFVRLIREMLD
QacR        MNL------KDKILGVAKELFIKNGYNATTGEIVKLSESSKGNLYHFKTKENL----FL----EILN cons          *:       ::  *:        *:      *.      *      *:::: **:   :*    *     :::

EilR        LDRLSRTALWFEQLFSALGSDDGRLEPYINVFRAQILADDDPEI---KSAYLLTMNLW--------
SmvR        AGQVPPPAWFAPLHAMLGSDDGRFEPYIDVFEAQILADRDPHI---RDAYLLTMDW---------
BRL6_KmrR   MPLVADDALWDERLFSMLGSDDGRLEPYIDVFEAQILADDDSDI---KDAYLLTMELD--------
QacR        I----EESKWQEQ---------------------WKKEQIRCKTNREKFYLYNELSLTTEYYYPLQNAIIEF cons                  : *:  :                                *::  *:   :.  :         **  ..:

EilR        ---------------HDEAVRQIRAGHAAGEFTIRDS----------------AENEAWR
SmvR        ---------------HEETVILILQGKQAGEFTFTAN----------------ATDEAWR
BRL6_KmrR   ---------------NETLKLIDRGTEAGEFTFKDH----------------AESEAWR
QacR        YTEYYKTNSINEKMNKLENKYIDAYHVIFKEGNLNGEWCINDVNAVSKIAANAVNGIVTFTHEQNINER cons                                          :   *:. *  **:                           .* *

EilR        LIRLVCGLDQIYVEGIPEVDDAAFTRHLQHVIQLELRS
SmvR        LIRLVCGLDQMYVEGIPEMADPAFKFHLDRHITLELKA
BRL6_KmrR   LIRLVCGLDQIYALGEEIDDATFNRHINYFISHELF
QacR        -IKLMNKFSQIFLNGLSK------------------- cons        * *:   :. ::: *:.:
```

Figure 14

SEQUENCE LISTING

```
<160> NUMBER OF SEQ ID NOS: 15

<210> SEQ ID NO 1
<211> LENGTH: 192
<212> TYPE: PRT
<213> ORGANISM: Enterobacter lignolyticus

<400> SEQUENCE: 1

Met Gly Tyr Leu Asn Arg Glu Glu Arg Arg Glu Thr Ile Met Gln Ala
1               5                   10                  15

Ala Met Arg Val Ala Leu Asp Gln Gly Phe Thr Gly Met Thr Val Arg
            20                  25                  30

Asn Ile Ala Thr Ala Ala Gly Val Ala Ala Gly Gln Val His His His
        35                  40                  45

Phe Thr Ser Ser Gly Glu Leu Lys Ser Gln Ala Phe Ile Arg Val Ile
    50                  55                  60

Arg Glu Met Met Asp Leu Gln Arg Leu Ser Arg Thr Ala Gly Trp Arg
65                  70                  75                  80

Glu Gln Leu Phe Ser Ala Leu Gly Ser Glu Asp Gly Arg Leu Glu Pro
                85                  90                  95

Tyr Ile Arg Leu Trp Arg Gln Ala Gln Leu Leu Ala Asp Ser Asp Pro
            100                 105                 110

Glu Ile Lys Ser Ala Tyr Leu Leu Thr Met Asn Leu Trp His Asp Glu
        115                 120                 125

Ala Val Arg Ile Ile Arg Ala Gly His Ala Ala Gly Glu Phe Thr Leu
    130                 135                 140

Arg Asp Ser Ala Glu Asn Ile Ala Trp Arg Leu Ile Ser Leu Val Cys
145                 150                 155                 160

Gly Leu Asp Gly Ile Tyr Val Leu Gly Met Pro Glu Val Asp Asp Ala
                165                 170                 175
```

```
Ala Phe Thr Arg His Leu Gln His Val Ile Gln Leu Glu Leu Phe Ser
            180                 185                 190
```

<210> SEQ ID NO 2
<211> LENGTH: 192
<212> TYPE: PRT
<213> ORGANISM: Salmonella typhimurium

<400> SEQUENCE: 2

```
Met Ser Tyr Leu Asn Arg Asp Glu Arg Arg Glu Val Ile Leu Gln Ala
1               5                   10                  15

Ala Met Arg Val Ala Leu Ala Glu Gly Phe Ala Ala Met Thr Val Arg
            20                  25                  30

Arg Ile Ala Ser Glu Ala Asp Val Ala Ala Gly Gln Val His His His
            35                  40                  45

Phe Ser Ser Ala Gly Glu Leu Lys Ala Leu Ala Phe Val His Leu Ile
    50                  55                  60

Arg Thr Leu Leu Asp Ala Gly Gln Val Pro Pro Pro Ala Thr Trp Arg
65                  70                  75                  80

Ala Arg Leu His Ala Met Leu Gly Ser Glu Asp Gly Phe Glu Pro
                85                  90                  95

Tyr Ile Lys Leu Trp Arg Glu Ala Gln Ile Leu Ala Asp Arg Asp Pro
            100                 105                 110

His Ile Arg Asp Ala Tyr Leu Leu Thr Met Gln Met Trp His Glu Glu
            115                 120                 125

Thr Val Thr Ile Ile Glu Gln Gly Lys Gln Ala Gly Glu Phe Thr Phe
            130                 135                 140

Thr Ala Asn Ala Thr Asp Ile Ala Trp Arg Leu Ile Ala Leu Val Cys
145                 150                 155                 160

Gly Leu Asp Gly Met Tyr Val Leu Gly Ile Pro Glu Met Ala Asp Pro
                165                 170                 175

Ala Phe Lys Tyr His Leu Asp Arg Met Ile Thr Leu Glu Leu Phe Ala
            180                 185                 190
```

<210> SEQ ID NO 3
<211> LENGTH: 191
<212> TYPE: PRT
<213> ORGANISM: Klebsiella sp. BRL6-2

<400> SEQUENCE: 3

```
Met Ser Tyr Leu Asn Arg Asp Ala Arg Arg Glu Val Ile Val Leu Ala
1               5                   10                  15

Ala Met Arg Val Ala Leu Arg Gly Gly Phe Ser Ala Met Thr Val Arg
            20                  25                  30

Asp Ile Ala Ala Glu Ala Gly Val Ser Ala Gly Gln Val His His His
            35                  40                  45

Phe Thr Ser Ala Gly Glu Leu Lys Ala His Thr Phe Val Arg Leu Ile
    50                  55                  60

Arg Glu Met Leu Asp Met Pro Leu Val Ala Asp Ala Thr Trp Arg
65                  70                  75                  80

Glu Arg Leu Phe Ser Met Val Gly Ser Asp Asp Gly Lys Leu Glu Pro
                85                  90                  95

Tyr Ile Arg Leu Trp Arg Glu Ala Gln Ile Leu Ala Asp Ser Asp Ser
            100                 105                 110

Asp Ile Lys Gly Ala Tyr Leu Leu Thr Met Ser Met Trp His Glu Glu
            115                 120                 125
```

```
Thr Leu Lys Ile Ile Gln Arg Gly Thr Glu Ala Gly Glu Phe Thr Pro
        130                 135                 140
Lys Asp His Ala Glu Ser Ile Ala Trp Arg Leu Ile Ala Leu Val Cys
145                 150                 155                 160
Gly Leu Asp Gly Ile Tyr Ala Leu Gly Met Glu Glu Ile Asp Asp Ala
                165                 170                 175
Thr Phe Asn Arg His Ile Asn Tyr Phe Ile Ser Met Glu Leu Phe
            180                 185                 190

<210> SEQ ID NO 4
<211> LENGTH: 188
<212> TYPE: PRT
<213> ORGANISM: Staphylococcus aureus

<400> SEQUENCE: 4

Met Asn Leu Lys Asp Lys Ile Leu Gly Val Ala Lys Glu Leu Phe Ile
1               5                   10                  15
Lys Asn Gly Tyr Asn Ala Thr Thr Thr Gly Glu Ile Val Lys Leu Ser
                20                  25                  30
Glu Ser Ser Lys Gly Asn Leu Tyr Tyr His Phe Lys Thr Lys Glu Asn
            35                  40                  45
Leu Phe Leu Glu Ile Leu Asn Ile Glu Glu Ser Lys Trp Gln Glu Gln
        50                  55                  60
Trp Lys Lys Glu Gln Ile Lys Cys Lys Thr Asn Arg Glu Lys Phe Tyr
65                  70                  75                  80
Leu Tyr Asn Glu Leu Ser Leu Thr Thr Glu Tyr Tyr Pro Leu Gln
                85                  90                  95
Asn Ala Ile Ile Glu Phe Tyr Thr Gly Tyr Tyr Lys Thr Asn Ser Ile
                100                 105                 110
Asn Glu Lys Met Asn Lys Leu Glu Asn Lys Tyr Ile Asp Ala Tyr His
            115                 120                 125
Val Ile Phe Lys Glu Gly Asn Leu Asn Gly Trp Cys Ile Asn Asp
        130                 135                 140
Val Asn Ala Val Ser Lys Ile Ala Ala Asn Ala Val Asn Gly Ile Val
145                 150                 155                 160
Thr Phe Thr His Glu Gln Asn Ile Asn Glu Arg Ile Lys Leu Met Asn
                165                 170                 175
Lys Phe Ser Gln Ile Phe Leu Asn Gly Leu Ser Lys
            180                 185

<210> SEQ ID NO 5
<211> LENGTH: 24
<212> TYPE: DNA
<213> ORGANISM: Enterobacter lignolyticus

<400> SEQUENCE: 5
caaactggac ggatgtccag cttt                                          24

<210> SEQ ID NO 6
<211> LENGTH: 24
<212> TYPE: DNA
<213> ORGANISM: Enterobacter lignolyticus

<400> SEQUENCE: 6
aaagctggac aagtgttcaa cttt                                          24

<210> SEQ ID NO 7
<211> LENGTH: 24
```

```
<212> TYPE: DNA
<213> ORGANISM: Enterobacter lignolyticus
<220> FEATURE:
<221> NAME/KEY: misc_feature
<222> LOCATION: (12)..(13)
<223> OTHER INFORMATION: n is a, c, g, or t

<400> SEQUENCE: 7
aaagttggac anntgtccaa cttt                                          24

<210> SEQ ID NO 8
<211> LENGTH: 62
<212> TYPE: DNA
<213> ORGANISM: Enterobacter lignolyticus

<400> SEQUENCE: 8
aaaagctgga caagtgttca actttccccc acgatcgcaa actggacgga tgtccagctt   60
tg                                                                  62

<210> SEQ ID NO 9
<211> LENGTH: 62
<212> TYPE: DNA
<213> ORGANISM: Enterobacter lignolyticus

<400> SEQUENCE: 9
aaaagctgga caagtgttca actttcccct ataatcgcaa actggacgga tgtccagctt   60
tg                                                                  62

<210> SEQ ID NO 10
<211> LENGTH: 62
<212> TYPE: DNA
<213> ORGANISM: Enterobacter lignolyticus

<400> SEQUENCE: 10
aaaagttgaa caagtgttca actttcccct ataatcgcaa actggacgga tgtccagctt   60
tg                                                                  62

<210> SEQ ID NO 11
<211> LENGTH: 26
<212> TYPE: DNA
<213> ORGANISM: TTATAGACCGATCGATCGGTCTATAA

<400> SEQUENCE: 11
ttatagaccg atcgatcggt ctataa                                        26

<210> SEQ ID NO 12
<211> LENGTH: 24
<212> TYPE: DNA
<213> ORGANISM: Enterobacter lignolyticus
<220> FEATURE:
<221> NAME/KEY: misc_feature
<222> LOCATION: (12)..(13)
<223> OTHER INFORMATION: n is a, c, g, or t

<400> SEQUENCE: 12
aaagttggac anntgtccaa cttt                                          24

<210> SEQ ID NO 13
<211> LENGTH: 24
<212> TYPE: DNA
<213> ORGANISM: Enterobacter lignolyticus

<400> SEQUENCE: 13
```

```
caaactggac ggatgtccag cttt                                              24
```

<210> SEQ ID NO 14
<211> LENGTH: 24
<212> TYPE: DNA
<213> ORGANISM: Enterobacter lignolyticus

<400> SEQUENCE: 14

```
aaagctggac aagtgttcaa cttt                                              24
```

<210> SEQ ID NO 15
<211> LENGTH: 178
<212> TYPE: PRT
<213> ORGANISM: Escherichia coli

<400> SEQUENCE: 15

```
Met Arg Arg Ala Asn Asp Pro Gln Arg Arg Glu Lys Ile Ile Gln Ala
1               5                   10                  15

Thr Leu Glu Ala Val Lys Leu Tyr Gly Ile His Ala Val Thr His Arg
            20                  25                  30

Lys Ile Ala Thr Leu Ala Gly Val Pro Leu Gly Ser Met Thr Tyr Tyr
        35                  40                  45

Phe Ser Gly Ile Asp Glu Leu Leu Glu Ala Phe Ser Ser Phe Thr
    50                  55                  60

Glu Ile Met Ser Arg Gln Tyr Gln Ala Phe Phe Ser Asp Val Ser Asp
65                  70                  75                  80

Ala Pro Gly Ala Cys Gln Ala Ile Thr Asp Met Ile Tyr Ser Ser Gln
                85                  90                  95

Val Ala Thr Pro Asp Asn Met Glu Leu Met Tyr Gln Leu Tyr Ala Leu
            100                 105                 110

Ala Ser Arg Lys Pro Leu Leu Lys Thr Val Met Gln Asn Trp Met Gln
        115                 120                 125

Arg Ser Gln Gln Thr Leu Glu Gln Trp Phe Glu Pro Gly Thr Ala Arg
    130                 135                 140

Ala Leu Asp Ala Phe Ile Glu Gly Met Thr Leu His Phe Val Thr Asp
145                 150                 155                 160

Arg Lys Pro Leu Ser Arg Glu Glu Ile Leu Arg Met Val Glu Arg Val
                165                 170                 175

Ala Gly
```

HOST CELLS AND METHODS USING A REPRESSOR POLYPEPTIDE AND AN INDUCIBLE PROMOTER FOR GENE EXPRESSION

RELATED PATENT APPLICATIONS

The application claims priority to U.S. Provisional Patent Application Ser. No. 62/187,767, filed Jul. 1, 2015, which is herein incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of production of inducible gene expression.

BACKGROUND OF THE INVENTION

An ionic liquid-resistance mechanism was recently identified in *Enterobacter lignolyticus* that consists of the EilA efflux pump, the EilR repressor and the intergenic regulatory DNA sequence (Nature Communications 5: 3490, and U.S. Patent Application Pub. No. 2014/0038848). EilR blocks transcription by binding to its operators (DNA binding sites) on the intergenic sequence. Ionic liquids act as inducer molecules by releasing EilR from the operators, enabling dynamic expression of the efflux pump in direct response to ionic liquids.

SUMMARY OF THE INVENTION

The present invention provides for a system comprising (a) a first nucleic acid comprising a nucleotide sequence encoding a nucleotide sequence of interest operatively linked to a promoter comprising a repressor polypeptide binding site, and (b) a second nucleic acid comprising a nucleotide sequence encoding a repressor polypeptide having at least 70% amino acid identity with EilR, SmvR, KmrR, RcdA, or QacR; wherein expression of the nucleotide sequence of interest from the promoter is induced by the presence of a hydrophobic inducer, such as a hydrophobic cation inducer, such as a triarylmethane, acridine, phenazine, phenothiazine, or xanthene, or a hydrophobic anion inducer.

This present invention provides for a system comprising (a) a first nucleic acid comprising a nucleotide sequence encoding a nucleotide sequence of interest operatively linked to a promoter comprising an EilR binding site or a QacR binding site, and (b) a second nucleic acid comprising a nucleotide sequence encoding a repressor polypeptide; with the proviso that (i) when the promoter comprises an EilR binding site, the repressor polypeptide comprises an amino acid sequence comprising a biologically active fragment having at least 70% amino acid identity with one of SEQ ID NO:1-3 and 15, and (ii) when the promoter comprises a QacR binding site, the repressor polypeptide comprises an amino acid sequence comprising a biologically active fragment having at least 70% amino acid identity with SEQ ID NO:4; and (i) when the repressor polypeptide has an amino acid sequence consisting of SEQ ID NO:1, the first and second nucleic acids are not the same nucleic acid and/or the nucleotide sequence of interest does not encode green fluorescence protein (GFP), and (ii) when the repressor polypeptide has an amino acid sequence consisting of SEQ ID NO:4, the first and second nucleic acids are not the same nucleic acid and/or the nucleotide sequence of interest does not encode chloramphenicol acetyltransferase (CAT); wherein expression of the nucleotide sequence of interest from the promoter is induced by the presence of the hydrophobic inducer, such as a hydrophobic cation inducer or a hydrophobic anion inducer. In some embodiments, the hydrophobic cation inducer is a triarylmethane, acridine, phenazine, phenothiazine, or xanthene. In some embodiments, the system is an in vitro system. In some embodiments, the system is an in vivo system.

The present invention also provides for a method for constructing a system or genetically modified host cell of the present invention. In some embodiments, the host cell is heterologous to the nucleotide sequence of interest, the EilR, SmvR, KmrR, or RcdA and/or the EilR binding site. In some embodiments, the host cell is heterologous to the nucleotide sequence of interest, the QacR, and/or the QacR binding site.

The present invention also provides for a genetically modified host cell comprising the system of the present invention.

The present invention also provides for method for expressing a nucleotide of interest comprising: (a) providing a system or genetically modified host cell of the present invention, (b) introducing a hydrophobic inducer to the system or genetically modified host cell, (c) expressing the nucleotide of sequence, or culturing or growing the genetically modified host cell such that nucleotide of interest is expressed, such that the nucleotide of interest is expressed at a rate higher when the hydrophobic inducer is present than if the hydrophobic inducer is not present in the system or genetically modified host cell. In some embodiments, wherein the expressing step (c) comprises expressing the polypeptide of interest.

BRIEF DESCRIPTION OF THE DRAWINGS

The foregoing aspects and others will be readily appreciated by the skilled artisan from the following description of illustrative embodiments when read in conjunction with the accompanying drawings.

FIG. 2 shows the amino acid sequence of EilR and DNA sequence of example eil-operators. The amino acid sequence of EilR depicted is SEQ ID NO:1. The nucleotide sequences of the eil operators depicted are SEQ ID NO:5-7. "n" is any nucleotide comprising any base, such as A, T, G, or C.

FIG. 3 shows a synthetic p1x Eil-promoter with two operator sites possesses increased strength and very low basal transcription activity. Addition of a second eil-operator drastically reduces basal expression while promoter strength increased 25% in the induced state.

FIG. 14 shows a simple multiple protein alignment of the amino acid sequences of EilR (SEQ ID NO:1), SmvR (SEQ ID NO:2), BRL6 KmrR (SEQ ID NO:3), and QacR (SEQ ID NO:4). Amino acid residues that are conserved for all four polypeptides is indicated by an "*". Amino acid residues that have a very strong conservation for all four polypeptides are indicated by an ":". Amino acid residues that have a strong conservation for all four polypeptides is indicated by an ".".

DETAILED DESCRIPTION OF THE INVENTION

Figure 1A:
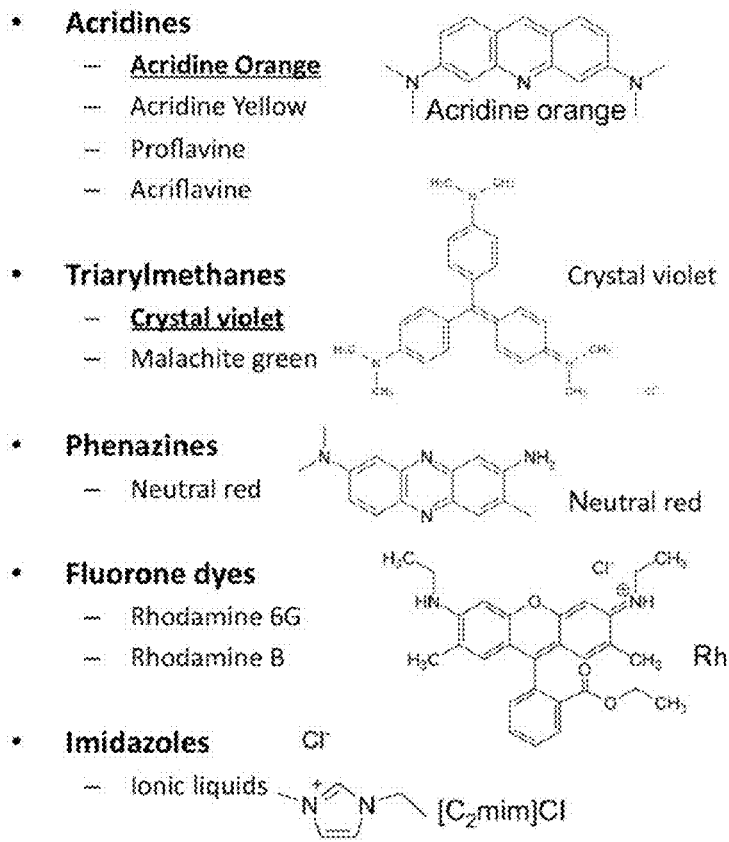
FIG. 1A shows the structures of some inducers molecules that induce Eil-promoters.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "heterologous" as used herein means that one component that is not found in nature with another component within the same organism.

In some embodiments, the system comprises (a) a first nucleic acid comprising a nucleotide sequence encoding a nucleotide sequence of interest operatively linked to a promoter comprising an EilR binding site, and (b) a second nucleic acid comprising a nucleotide sequence encoding a repressor polypeptide comprising an amino acid sequence comprising a biologically active fragment having at least 70% amino acid identity with one of SEQ ID NO:1-3 and 15; with the proviso that when the repressor polypeptide has an amino acid sequence consisting of SEQ ID NO:1, the first and second nucleic acids are not the same nucleic acid and/or the nucleotide sequence of interest does not encode green fluorescence protein (GFP).

In some embodiments, the system comprises (a) a first nucleic acid comprising a nucleotide sequence encoding a nucleotide sequence of interest operatively linked to a promoter comprising a QacR binding site, and (b) a second nucleic acid comprising a nucleotide sequence encoding a repressor polypeptide comprising an amino acid sequence comprising a biologically active fragment having at least 70% amino acid identity with SEQ ID NO:4; with the proviso that when the repressor polypeptide has an amino acid sequence consisting of SEQ ID NO:4, the first and second nucleic acids are not the same nucleic acid and/or the nucleotide sequence of interest does not encode chloramphenicol acetyltransferase (CAT).

The amino acid sequence of *E. coli* RcdA is as follows:

```
                                             (SEQ ID NO: 15)
         10          20          30          40
   MRRANDPQRR  EKIIQATLEA  VKLYGIHAVT  HRKIATLAGV 50          60          70          80
   PLGSMTYYFS  GIDELLLEAF  SSFTEIMSRQ  YQAFFSDVSD 90         100         110         120
   APGACQAITD  MIYSSQVATP  DNMELMYQLY  ALASRKPLLK 130         140         150         160
   TVMQNWMQRS  QQTLEQWFEP  GTARALDAFI  EGMTLHFVTD

170
   RKPLSREEIL  RMVERVAG
```

In some embodiments, the repressor polypeptide comprises an amino acid sequence comprising a biologically active fragment having at least 75%, 80%, 85%, 90%, 95%, or 99% amino acid identity with one of SEQ ID NO:1-4 and 15. In some embodiments, the repressor polypeptide comprises an amino acid sequence comprising a biologically active fragment having identity with one of SEQ ID NO:1-4 and 15. In some embodiments, the repressor polypeptide comprises an amino acid sequence consisting of one of SEQ ID NO:1-4 and 15. A biologically active fragment of the repressor polypeptide is a polypeptide capable of binding to an EilR binding site (or eilO or eil operator) or a QacR binding site, and in the presence of the hydrophobic inducer binds to the hydrophobic inducer and does not binding to the EilR binding site or the QacR binding site. The EilR binding site is capable of being bound by the wild-type EilR in the absence of the hydrophobic inducer. The QacR binding site is capable of being bound by the wild-type QacR in the absence of the hydrophobic inducer. Suitable EilR binding sites are:

```
                                          (SEQ ID NO: 12)
            AAAGTTGGACANNTGTCCAACTTT (SEQ ID NO: 13)
            CAAACTGGACGGATGTCCAGCTTT (SEQ ID NO: 14)
            AAAGCTGGACAAGTGTTCAACTTT
```

In some embodiments, the EilR binding site comprises the nucleotide sequence of one of: SEQ ID NO:5-7 and 12-14; the underlined nucleotide sequences of SEQ ID NO:8-10; and one of the EilR bindings sites of the p1x promoter. In some embodiments, the QacR binding site comprises the nucleotide sequence of SEQ ID NO:11. The EilR binding site or the QacR binding site when adjacent to or near or between the −35 and/or −10 sites of a promoter, or the consensus sites of any promoter, which, when bound by EilR or QacR, prevent initiation or binding by a RNA polymerase to the promoter, or prevent transcription from the promoter. The promoter can be a eukaryotic promoter, such as fungal promoter, such as a yeast promoter, a mammalian promoter, an insect promoter, or a plant promoter, a prokaryotic promoter, such as eubacterial promoter or an archaeal promoter.

In some embodiments, the repressor polypeptide comprises an amino acid sequence comprising one, two, three, four, five, six, seven, or eight of the conserved amino acid residues indicated by an "*" in FIG. 14. In some embodiments, the repressor polypeptide comprises an amino acid sequence comprising one, two, three, four, five, six, seven, or eight of any of the conserved amino acid residues indicated by an ":" and/or "." in FIG. 14; for example, the amino acid residue at position 2 can be G, S, or N. In some embodiments, the repressor polypeptide comprises an amino acid sequence comprising a biologically active fragment having at least 70% amino acid identity with one of SEQ ID NO:1-4 and 15, and further comprising one, two, three, four, five, six, seven, or eight of the conserved amino acid residues indicated by the rectangular boxes in FIG. 14.

In some embodiments, the biologically active fragment of EilR comprises a polypeptide comprising an amino acid sequence having at least 70% amino acid identity with an amino acid sequence of EilR, such as SEQ ID NO:1. A biologically active fragment of EilR is a polypeptide that is capable of binding an EilR binding site such that transcription from a promoter comprising the EilR binding site is reduced or repressed, and the polypeptide does not bind the EilR binding site in the presence of the hydrophobic inducer.

In some embodiments, the EilR binding site comprises the nucleotide sequence of SEQ ID NO:7. In some embodiments, the EilR binding site comprises the nucleotide sequence of SEQ ID NO:5 or 6. In some embodiments, the promoter comprising an EilR binding site, or QacR binding site, comprises a first EilR binding site, or QacR binding site, is located adjacent to or between one or more DNA binding sites of RNA polymerase such that transcription from the promoter is reduced or repressed in the presence of EilR, SmvR, KmrR, or RcdA (or QacR). In some embodiments, the promoter is a −35/−10 promoter, wherein the promoter comprising an EilR binding site, or QacR binding site, comprises a first EilR binding site, or QacR binding site, is located between a −35 nucleotide sequence and a −10 nucleotide sequence. In some embodiments, the promoter comprising an EilR binding site, or QacR binding site, further comprises a second EilR binding site located 3' to the −10 nucleotide sequence. In some embodiments, the second EilR binding site, or QacR binding site, is directly adjacent to the −10 nucleotide sequence.

Figure 15:
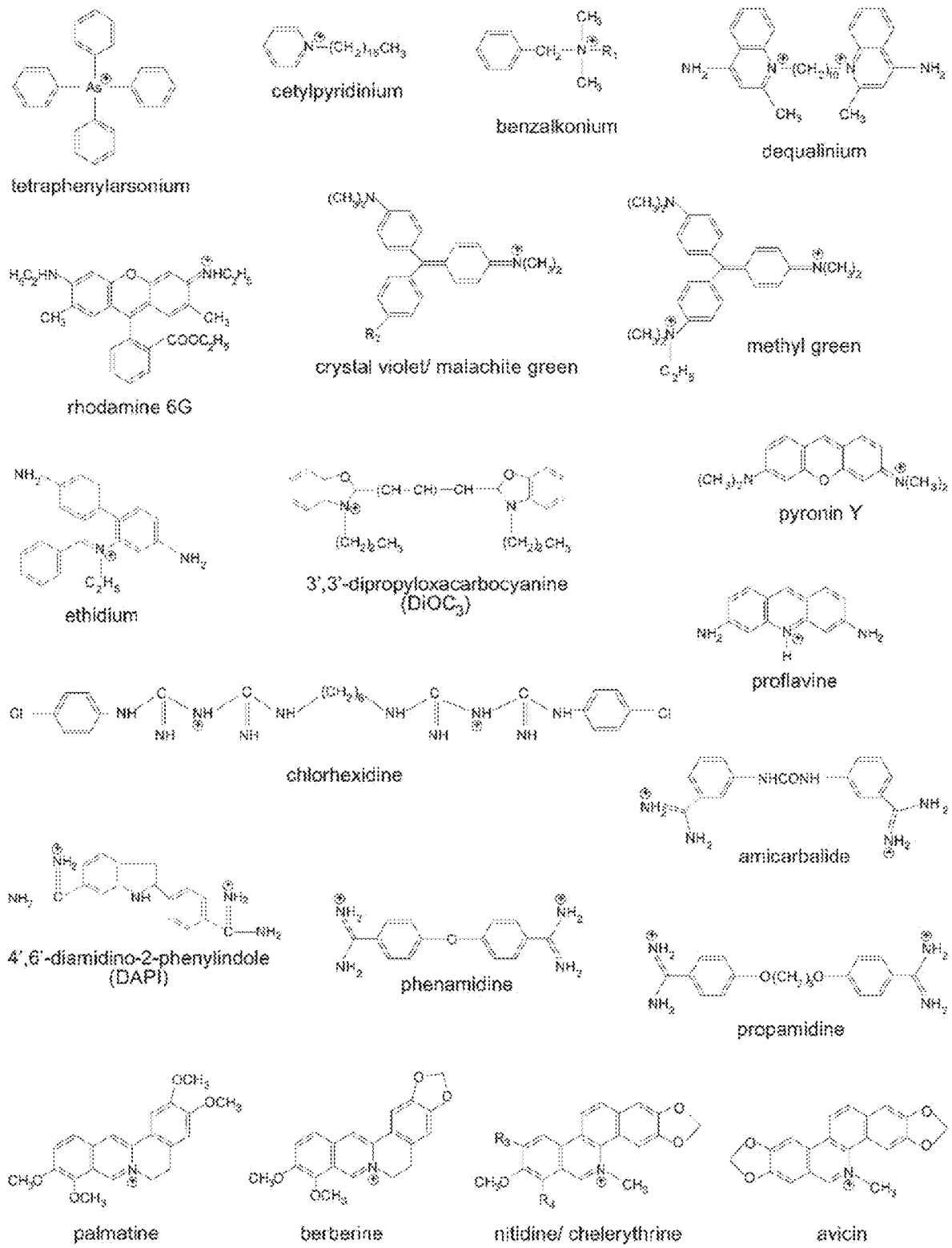
FIG. 15 shows the chemical structures of inducer compounds useful for the present invention. Depicted are the monovalent Qacs tetraphenylarsonium, cetylpyridinium, and benzalkonium ($R_1$=—$C_{12}H_{25}$, —$C_{14}H_{29}$, or —$C_{16}H_{33}$), the bivalent Qac dequalinium, the monovalent dyes rhodamine 6G, crystal violet [$R_2$=—$N(CH_3)_2$], malachite green ($R_2$=—H), ethidium, $DiOC_3$, pyronin Y, and proflavin, the bivalent dye methyl green, the bivalent guanidine chlorhexidine, the bivalent diamidines amicarbalide, DAPI, phenamidine, and propamidine, and the plant alkaloids palmatine, berberine, nitidine ($R_3$=—$OCH_3$, $R_4$=—H), chelerythrine ($R_3$=—H, $R_4$=—$OCH_3$), and avicin.

The hydrophobic inducer is a hydrophobic cation inducer or a hydrophobic anion inducer. The hydrophobic cation inducer comprises an organic molecule comprising a cation, such as $N^+$ or $As^+$, and one or more ring structure. The ring structure is a benzene, or a heterocyclic ring structure, such as a pyridine, pyrazole, imidizole, isoxazole, or the like. In some embodiments, organic molecule comprises two or more, three or more, or four or more fused or not fused ring structures. In some embodiments, organic molecule comprises one, two, three, or four aromatic ring structures. In some embodiments, organic molecule comprises two, three, or four aromatic ring structures fused together. In some embodiments, the aromatic ring structure comprises a heteroatom, such as N or O. In some embodiments, the heteroatom is an ammonium cation (N⁺). In some embodiments, the system further comprises a hydrophobic cation inducer. In some embodiments, the hydrophobic cation inducer comprises an ammonium (N⁺) or arsenate (As⁺). In some embodiments, the hydrophobic cation inducer is an ionic liquid (IL). In some embodiments, the system further comprises a hydrophobic cation inducer, such as one or more of an acridine, triarylmethane, phenazine, imidazole, phenanthridine, fluorine, phenothiazine, phenazine, xanthene, or a mixture thereof. In some embodiments, the hydrophobic cation inducer is any compound depicted or listed in FIG. 1A and/or FIG. 15. In some embodiments, the hydrophobic cation inducer has a molecular weight equal to or greater than the molecular weight of any of the compounds depicted or listed in FIG. 1A and/or FIG. 15. In some embodiments, the hydrophobic cation inducer is xenobiotic and does not interfere with the metabolism of the host cell.

The following are suitable hydrophobic cation inducers: acridines, triarylmethanes, phenazines, imidazoles, phenanthridines, and fluorones. Further useful hydrophobic cation inducers are: quinolines (such as, dequalinium) and pyridines (such as, cetylpyridinium or the bipyridinium cation methyl viologen). The following are suitable hydrophobic cation inducers: tetraphenylarsonium, cetylpyridinium, benzalkonium, dequalinium, rhodamine, crystal violet, malachite green, ethidium, pyronin Y, proflavin, methyl green, guanidine chlorhexidine, diamidines amicarbalide, DAPI, phenamidine, propamidine, palmatine, berberine, nitidine, chelerythrine, and avicin.

In some embodiments, the IL is any suitable IL comprising an imidazole or pyrazole, or a mixture thereof, described herein. Suitable IL are taught in ChemFiles (2006) 6(9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

Suitable IL include, but are limited to, 1-ethyl-3-methylimidazolium acetate (EMIN Acetate), 1-ethyl-3-methylimidazolium chloride (EMIM Cl), 1-ethyl-3-methylimidazolium hydrogensulfate (EMIM HOSO₃), 1-ethyl-3-methylimidazolium methylsulfate (EMIM MeOSO₃), 1-ethyl-3-methylimidazolium ethylsulfate (EMIM EtOSO₃), 1-ethyl-3-methylimidazolium methanesulfonate (EMIM MeSO₃), 1-ethyl-3-methylimidazolium tetrachloroaluminate (EMIM AlCl₄), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO₃), 1-butyl-3-methylimidazolium methanesulfonate (BMIM MeSO₃), 1-butyl-3-methylimidazolium methylsulfate (BMIM MeOSO₃), 1-butyl-3-methylimidazolium tetrachloroaluminate (BMIM AlCl₄), 1-butyl-3-methylimidazolium thiocyanate (BMIM SCN), 1-ethyl-2,3-dimethylimidazolium ethylsulfate (EDIM EtOSO₃), Tris (2-hydroxyethyl)methylammonium methylsulfate (MTEOA MeOSO₃), 1-methylimidazolium chloride (MIM Cl), 1-methylimidazolium hydrogensulfate (MIM HOSO₃), 1,2,4-trimethylpyrazolium methylsulfate, and the like.

In some embodiments, the hydrophobic anion inducer comprises an organic molecule comprising one or more ring structure. In some embodiments, the hydrophobic anion inducer is a quinoline, triarylmethane (such as crystal violet), azo-dye, or a xanthene, such as erythrosine.

In some embodiments, the hydrophobic anion inducer is non-toxic. The ring structure is a benzene, or a heterocyclic ring structure, such as a pyridine, pyrazole, imidizole, isoxazole, or the like. In some embodiments, the organic molecule comprises two or more, three or more, or four or more fused or not fused ring structures. In some embodiments, the organic molecule comprises one, two, three, or four aromatic ring structures. In some embodiments, the organic molecule comprises two, three, or four aromatic ring structures fused together. In some embodiments, the aromatic ring structure comprises a heteroatom, such as N. In some embodiments, the system further comprises a hydrophobic anion inducer.

Figure 16:
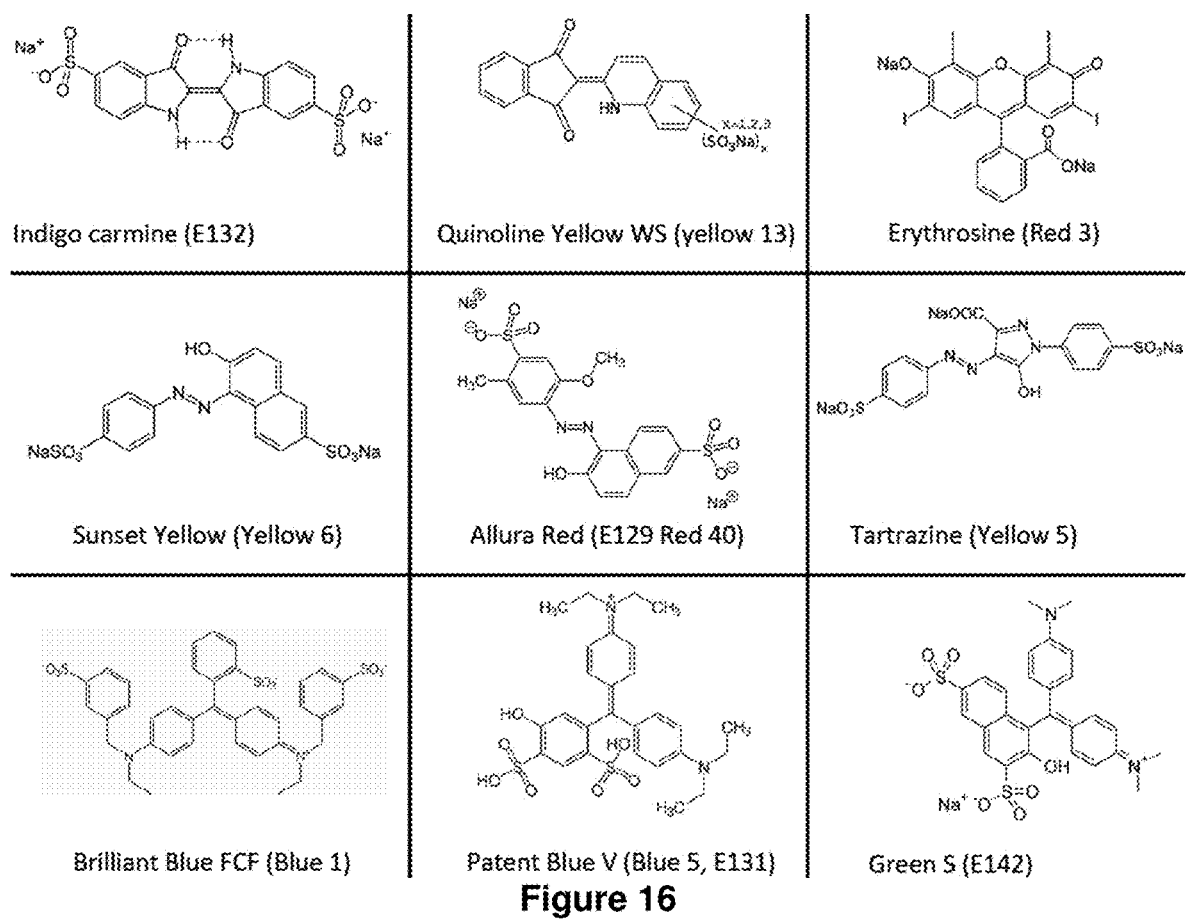
FIG. 16 shows the chemical structures of inducer compounds useful for the present invention. Depicted are indigo carmine (E132), quinolone yellow WS (Yellow 13), erythrosine (Red 3), sunset yellow (Yellow 6), alura red (E129 Red 40), tartrazine (Yellow 5), brilliant blue FCF (Blue 1), patent blue V (Blue 5, E131), and green S (E142).

In some embodiments, the hydrophobic anion inducer is a non-toxic food coloring compound, such as indigo carmine (E132), quinolone yellow WS (Yellow 13), erythrosine (Red 3), sunset yellow (Yellow 6), alura red (E129 Red 40), tartrazine (Yellow 5), brilliant blue FCF (Blue 1), patent blue V (Blue 5, E131), and green S (E142) (shown in FIG. 16).

In some embodiments, the first nucleic acid and the second nucleic acid are the same molecule. In some embodiments, the first nucleic acid and the second nucleic acid are separate molecules.

In some embodiments, the nucleotide sequence of interest is heterologous to EilR, SmvR or KmrR, the EilR binding site, and/or the host cell. In some embodiments, the EilR, SmvR or KmrR is heterologous to the host cell. In some embodiments, the nucleotide sequence of interest is heterologous to QacR, the QacR binding site, and/or the host cell. In some embodiments, the QacR is heterologous to the host cell.

In some embodiments, the nucleotide sequence of interest encodes one or more open reading frames (ORFs), each encoding a polypeptide of interest. In some embodiments, each polypeptide of interest is an enzyme. In some embodiments, the nucleotide sequence of interest encodes one or more enzymes involved in the production of one or more biofuel from a sugar carbon source.

In some embodiments, the invention comprises the eilR repressor gene and the native or modified eil-operators engineered to promoters that can be induced by a range of hydrophobic cations. De novo design of synthetic promoters containing eil-operators as well as modifications of the native regulatory DNA region generated a set of highly sensitive promoters that are inducible over several orders of magnitude.

Eil-promoters enable high expression rates when induced while basal transcription levels are minimal in the repressed state. The low costs for full induction (less than one dollar for a 1000 L culture) make this present invention particularly suitable for large scale industrial applications. The eil-promoters do not require special media conditions (e.g. glucose for catabolite repression) and were shown to function in a variety of bacteria.

A series of EilR-regulated promoters have been identified by creating a library that contains an eil-operator and randomized core promoter sequences coupled to a reporter gene. By testing one of these promoters with several hydrophobic ammonium cations, it is found that nanomolar to low micromolar concentrations of acridines or triarylmethanes are sufficient for full induction. Subsequent optimizations have led to several Eil-promoters with improved properties.

Besides the mentioned Eil-promoters, the present invention includes the use of a range of hydrophobic cations (e.g. perature sensitive promoters. Each of those promoters have benefits and drawbacks (e.g. high cost of inducer molecules, leakiness, restriction to a certain media or host strain). See Table 1.

TABLE 1

Common *E. coli* promoter systems for heerologous protein production and their characteristics.

| Expression system based on | Induction (range of inductor) | Level of expression | Key features | Original reference |
|---|---|---|---|---|
| lac promoter | Addition of IPTG 0.2 mM (0.05-2.0 mM) | Low level up to middle | Weak, regulated suitable for gene products at very low intracellular level Comparatively expensive induction | Gamenborn (1976) |
| trc and tac promoter | Addition of IPTG 0.2 mM (0.05-2.0 mM) | Moderately high | High-level, but lower than T7 system Regulated expression still possible Comparatively expensive induction High basal level | Brosius et al. (1985) |
| T7 RNA polymerase | Addition of IPTG 0.2 mM (0.05-2.0 mM) | Very high | Utilizes T7 RNA polymerase High-level inducible over expression T7lac system for tight control of induction needed for more toxic clones Relative expensive induction Basal level depends on used strain (pLys) | Studier and Moffiett (1986) |
| Phage promoter $p_L$ | Shifting the temperature from 30 to 42° C. (45° C.) | Moderately high | Temperature-sensitive host required Less likelihood of "leaky" uninduced expression Basal level, high basal level by temperatues below 30° C. No inducer | Elvin et. al. (1990) |
| tetA promoter/operator | Anhydrotetracycline 200 µg/l | Variable from middle to high level | Tight regulation Independent on metabolic state Independent on *E. coli* strain Relative inexpensive inducer Low basal level | Skerra (1994) |
| araBAD promoter ($P_{BAD}$) | Addition of L-arabinose 0.2% (0.001-1.0%) | Variable from low to high level | Can fine-tune expression levels in a dose-dependent manner Tight regulation possible Low basal level Inexpensive inducer | Guzman et al. (1995) |
| rhaP$_{BAD}$ promoter | t-rhamnose 0.2% | Variable from low to high level | Tight regulation Low basal activity Relative expensive inducer | Haldimann et al. (1998) | chemical dyes like acridines, triarylmethanes, see FIG. 1A) as inducers for gene expression in general. The high binding affinity of these inexpensive compounds to EilR and other transcriptional regulators, such as SmvR and KmrR (FIG. 12) enables efficient release of the regulatory protein from its DNA-binding site at low concentrations.

One or more purposes of using the repressor together with its operator to engineer synthetic promoters include, but are not limited to: (a) for its characterization, which includes the development of a reporter coupled biosensor as a tool to detect additional/natural inducer molecules; (b) to provide a set of inducible promoters of varied strength for a potential use in biofuel applications (e.g. to express other tolerance mechanisms or enzymes in the presence of ionic liquid pretreated biomass).

In some embodiments, when testing one of the developed biosensors with other substrates of the EilA efflux pump, a range of hydrophobic cations can strongly induce this sensor at very low concentrations.

In some embodiments, the present invention comprises a controlled and highly inducible EilR-based (or QacR-based) expression systems by combining core promoters with eil-operators (or qac-operators). In some embodiments, the present invention can be practiced using inducing molecules that induce the engineered promoters at low concentrations.

There are numerous *E. coli* expression systems using inducible promoters for gene expression, such as the LacI/IPTG, Tet/tetracyclines or AraC/arabinose systems or tem- The present invention comprises one or more of the following components:

(1) Sequences encoding the EilR protein together with its DNA binding sites (eilO operators) to induce and regulate gene transcription from prokaryotic, eukaryotic and archaeal promoters.

(2) Hydrophobic cations (e.g. acridines, triarylmethanes, phenazines, imidazoles, phenanthridines, fluorones) as inducers for gene expression.

The system can be applied to various host cells and various promoters. For example, integration of eil-operators into phage promoters (e.g. from T5, Lambda, T7) can boost expression rates even higher. Altering self-regulated expression of EilR increases the dynamic range for finely titratable promoters. Efficiency of the Eil-system in other bacterial hosts can be increased by taking into account their native promoter structure.

The Eil-system (or QacR-system) can be introduced into a eukaryotic host cell by retaining the function of EilR (or QacR) as a repressor, and introduced into eukaryotic cells so as to use EilR (or QacR) as a transactivator for tuning eukaryotic promoters. Similar to the Tet-ON system, a mutated EilR (or QacR) transactivator can reverse its binding properties, so that it is only bound to its operator in the presence of an inducer, thereby activating eukaryotic promoter. In some embodiments, the eukaryotic host cell is a fungal (such as yeast), mammalian, insect, or plant host cell.

In some embodiments, the eukaryotic promoter is a fungal (such as yeast), mammalian, insect, or plant promoter.

The QacR repressor is well-characterized and is shown to bind to many of the EilR ligands. The QacR DNA binding site is as follows: TTATAGACCGATCGATCGGTCTATAA (SEQ ID NO:11). The amino acid sequence of QacR is as follows:

```
                                          (SEQ ID NO: 4)
MNLKDKILGVAKELFIKNGYNATTTGEIVKLSESSKGNLY

YHFKTKENLFLEILNIEESKWQEQWKKEQIKCKTNREKFY

LYNELSLTTEYYYPLQNAIIEFYTEYYKTNSINEKMNKLE

NKYIDAYHVIFKEGNLNGEWCINDVNAVSKIAANAVNGIV

TFTHEQNINERIKLMNKFSQIFLNGLSK
```

The present invention is also useful for the following applications:

The Eil- or Qac-Promoters are Useful as Biosensors.

Some inducer compounds such as Malachite Green are used in fish farms as antimicrobial agents. Imported fish to the U.S. needs to be analyzed for trace amounts of these agents. The high sensitivity of an Eil-biosensor to these molecules might serve as a method for their easy detection.

The Eil- or Qac-Promoters are Useful as Tools for Monitoring Real Time Oxidative Stress.

While crystal violet induces Eil-promoters at nanomolar concentrations, preliminary results indicate that its uncharged, reduced leuco-form does not cause induction. Free radicals possess the ability to oxidize leucocrystal violet to its inducing cation, crystal violet. An Eil-promoter or Qac-promoter coupled with a reporter gene can serve as a signal-amplifying sensor for real time in vivo oxidative stress, which could be useful to monitor and understand physiological stress reactions. Similarly, heme catalyzes the oxidation of the colorless leucocrystal violet to its purple cation by reducing hydrogen peroxide. This colorful radical reaction is utilized in forensics to uncover removed blood stains. Crystal violet induces Eil-biosensors at concentrations that are much lower than the eye can detect. Such a sensor could be a sensitive tool for blood detection in forensic analyses.

In some embodiments, the host cell is yeast. Yeast host cells suitable for practice of the methods of the invention include, but are not limited to, *Yarrowia, Candida, Bebaromyces, Saccharomyces, Schizosaccharomyces* and *Pichia*, including engineered strains provided by the invention. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis, C. zeylenoides*, and *C. tropicalis*.

In some embodiments the host cell is a bacterium. Bacterial host cells suitable for practice of the methods of the invention include, but are not limited to, *Escherichia, Bacillus, Salmonella, Klebsiella, Enterobacter, Pseudomonas, Streptomyces, Cynechocystis, Cynechococcus, Sinorhizobium*, and *Caulobacter*, including engineered strains provided by the invention.

One can modify the expression of a gene encoding any of the enzymes taught herein by a variety of methods in accordance with the methods of the invention. Those skilled in the art would recognize that increasing gene copy number, ribosome binding site strength, promoter strength, and various transcriptional regulators can be employed to alter an enzyme expression level.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Figure 1B:
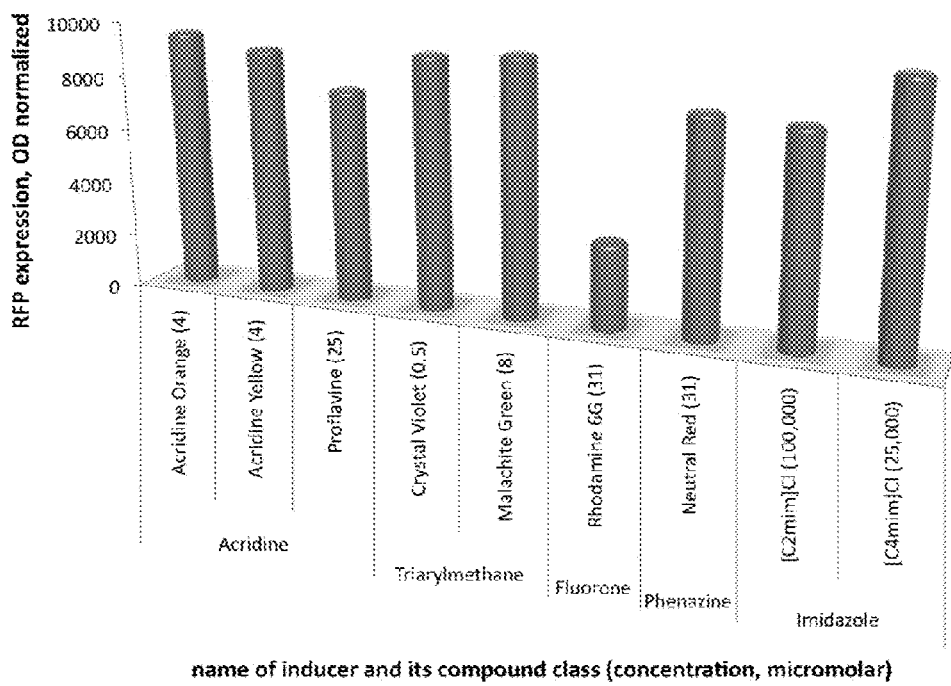
FIG. 1B shows induction by different hydrophobic cation inducers. Induction of an Eil-promoter by a range of cationic dyes. Numbers in brackets indicate the concentration applied for induction (in µM).

FIG. 1B shows the induction of an Eil-promoter by a range of cationic dyes. Numbers in brackets indicate the concentration applied for induction (in μM).

Figure 4:
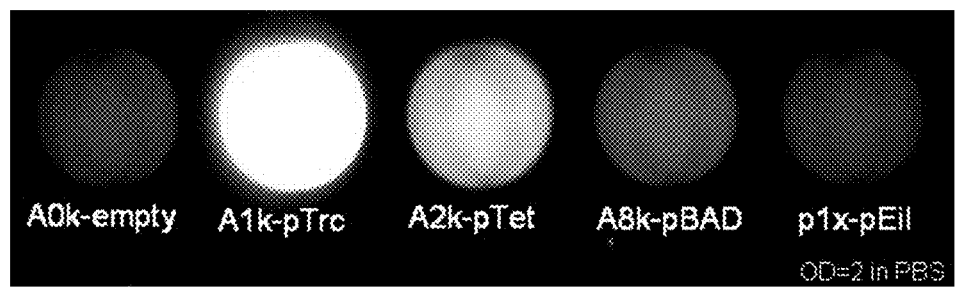
FIG. 4 show an extremely low basal transcription level. The p1x Eil-promoter outperforms inducible systems that are known for their tightness such as pTet and pBAD. RFP fluorescence of OD-normalized stationary phase *E. coli* DH10B cultures grown in terrific broth. The image was taken in a Gel-imager (Cy3 filter). All plasmids contain the same RBS and origin of replication (p15A).

FIG. 3 shows a very low basal activity in the absence of the inducer. For example, repression of the p1x Eil-promoter is superior to the tightly regulated pTet and pBAD promoters. FIG. 3 shows a synthetic p1x Eil-promoter with two operator sites possesses increased strength and very low basal transcription activity. Addition of a second eil-operator drastically reduces basal expression while promoter strength increased 25% in the induced state. FIG. 4 show an extremely low basal transcription level. The p1x Eil-promoter outperforms inducible systems that are known for their tightness such as pTet and pBAD. RFP fluorescence of OD-normalized stationary phase *E. coli* DH10B cultures grown in terrific broth. The image was taken in a Gel-imager (Cy3 filter). All plasmids contain the same RBS and origin of replication (p15A).

Figure 5A:
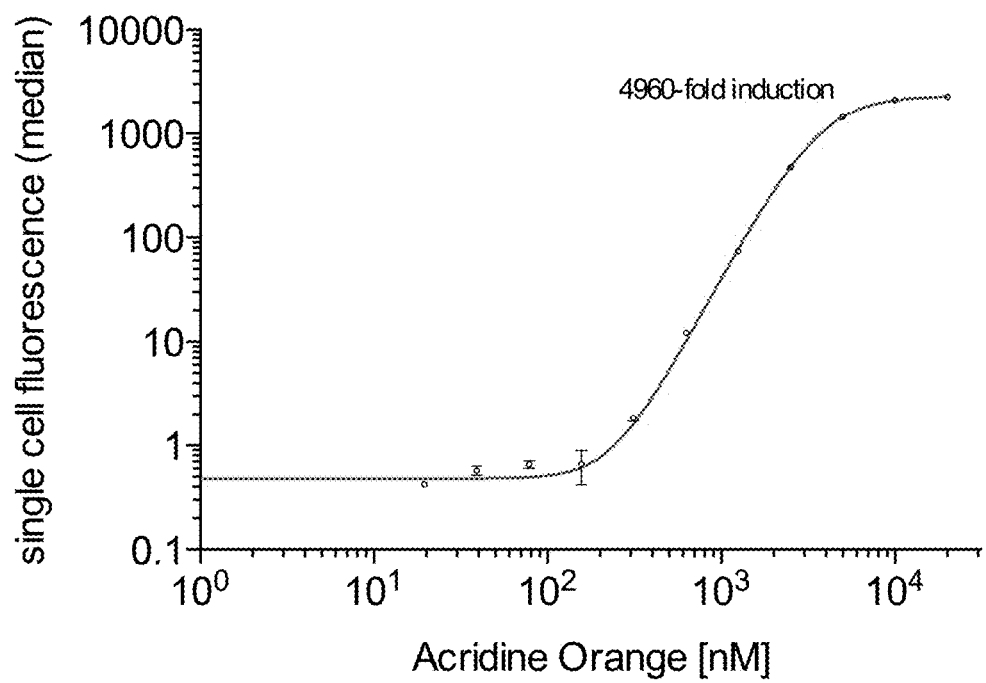
FIG. 5A shows a high induction range of p1x Eil-promoter. Fluorescence measurements by more sensitive flow cytometry show that the p1x promoter possesses an induction range over 4 to 5 orders of magnitude.
Figure 5B:
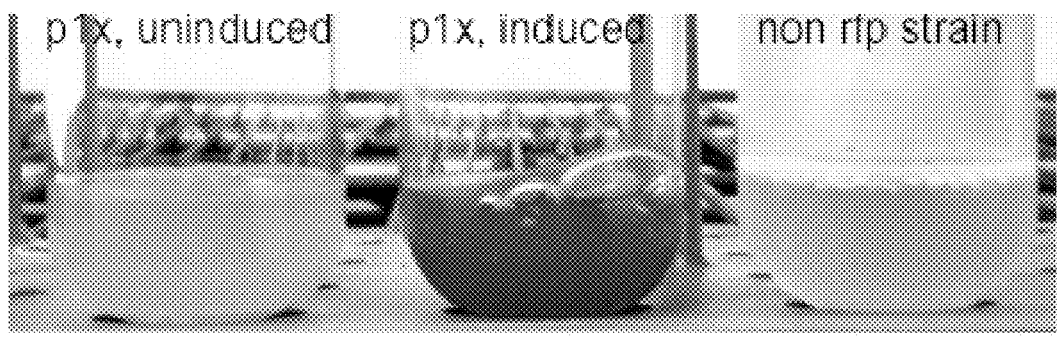
FIG. 5B shows a high induction range of p1x Eil-promoter. RFP expression in uninduced and induced cultures grown in terrific broth to stationary phase. The strength of p1x is similar to the pTrc promoter.

FIGS. 5A and 5B shows a high induction range of p1x Eil-promoter. FIG. 5A shows fluorescence measurements by more sensitive flow cytometry show that the p1x promoter possesses an induction range over 4 to 5 orders of magnitude. FIG. 5B shows RFP expression in uninduced and induced cultures grown in terrific broth to stationary phase. The strength of p1x is similar to the pTrc promoter.

Figure 6:
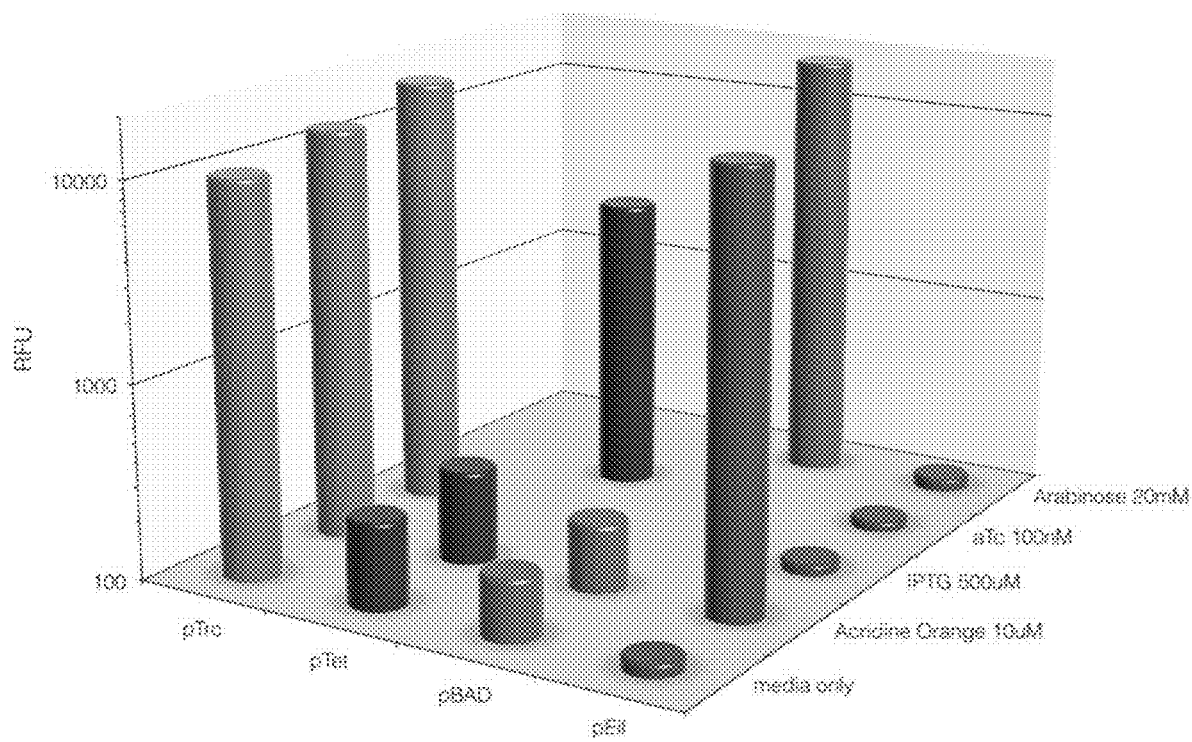
FIG. 6 shows orthogonality of p1x Eil-promoter and its inducer—no interference with other promoters. Fluorescence of E. coli cells expressing RFP from common inducible promoters. Cultures were induced in early log-phase (OD=1.3) and grown to stationary phase in terrific broth for 21 hours. E. coli background fluorescence was not deducted in this figure.

FIG. 6 shows orthogonality of p1x Eil-promoter and its inducer. They do not interfere with other promoters and other induction systems (such as, pBAD/arabinose, pTet/anhydrotetracycline, pTrc/IPTG). Fluorescence of *E. coli* cells expressing RFP from common inducible promoters. Cultures were induced in early log-phase (OD=1.3) and grown to stationary phase in terrific broth for 21 hours. *E. coli* background fluorescence was not deducted in this figure.

Figures 7A, 7B:
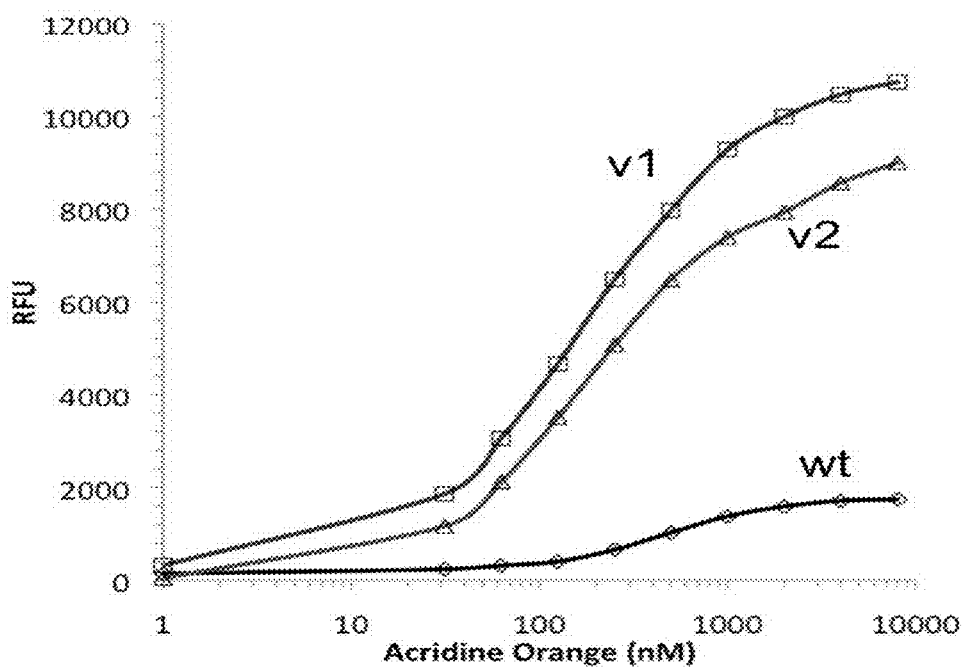
FIG. 7A shows modifications in the core promoter regions of the eilAR intergenic sequence increases promoter strength. The eilA-efflux pump gene was replaced with rfp while the upstream intergenic region and the eilR repressor gene were kept. Basepairs labeled in red indicate modifications in the −35 and the −10 regions of the E. lignolyticus wild-type eilA promoter (wt). The nucleotide sequences are from top to bottom: SEQ ID NO:8-10.
FIG. 7B shows modifications in the core promoter regions of the eilAR intergenic sequence increases promoter strength. The modified versions (v1 and v2) result in increased RFP expression compared to the wild-type.

FIGS. 7A and 7B shows modifications in the core promoter regions of the eilAR intergenic sequence increases promoter strength. FIG. 7A shows the eilA-efflux pump gene was replaced with rfp while the upstream intergenic region and the eilR repressor gene were kept. Basepairs labeled in red indicate modifications in the −35 and the −10 regions of the *E. lignolyticus* wild-type eilA promoter (wt). The nucleotide sequences are from top to bottom: SEQ ID NO:8-10. FIG. 7B shows the modified versions (v1 and v2) result in increased RFP expression compared to the wild-type.

Figure 8:
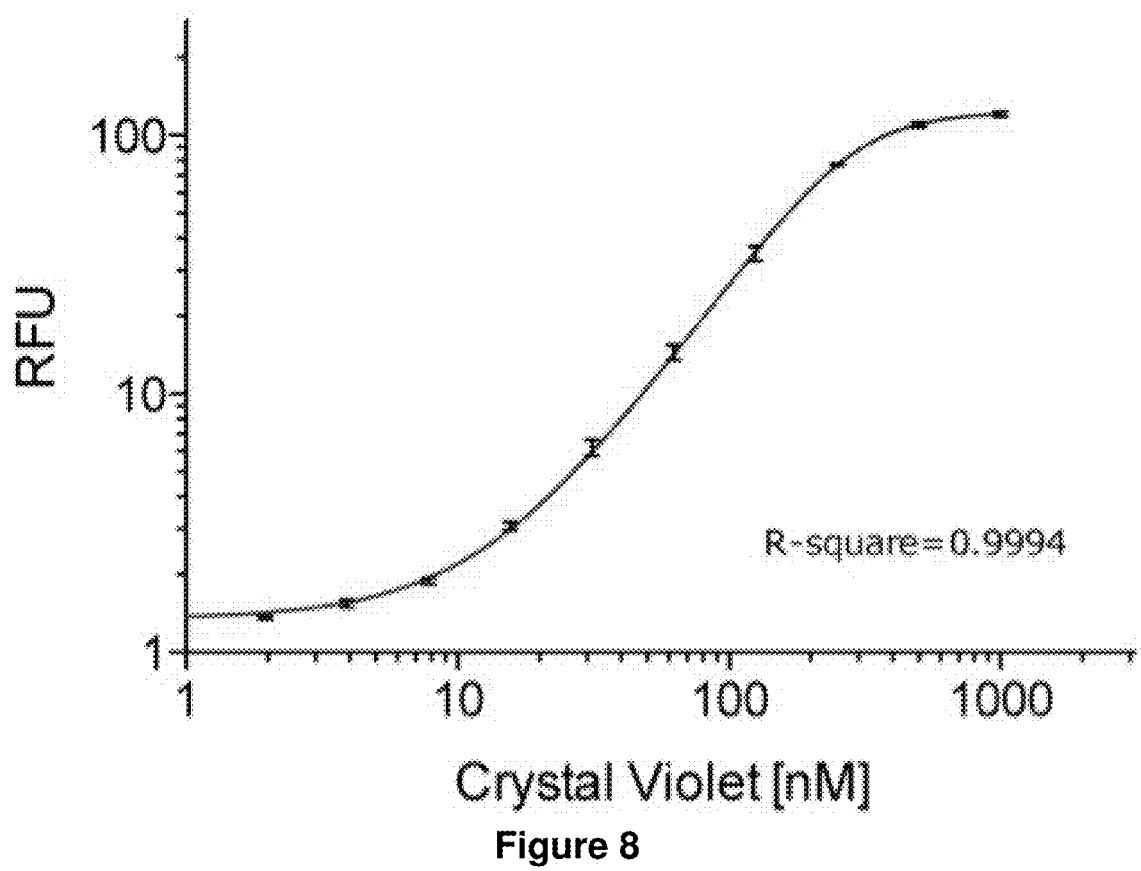
FIG. 8 shows EilR repressor autoregulation enables wide dynamic range at nanomolar inducer concentrations. Such a promoter is useful for titratable gene expression and as a biosensor.

FIG. 8 shows EilR repressor autoregulation enables wide dynamic range at nanomolar inducer concentrations. Such a promoter is useful for titratable gene expression and as a biosensor.

Figure 9:
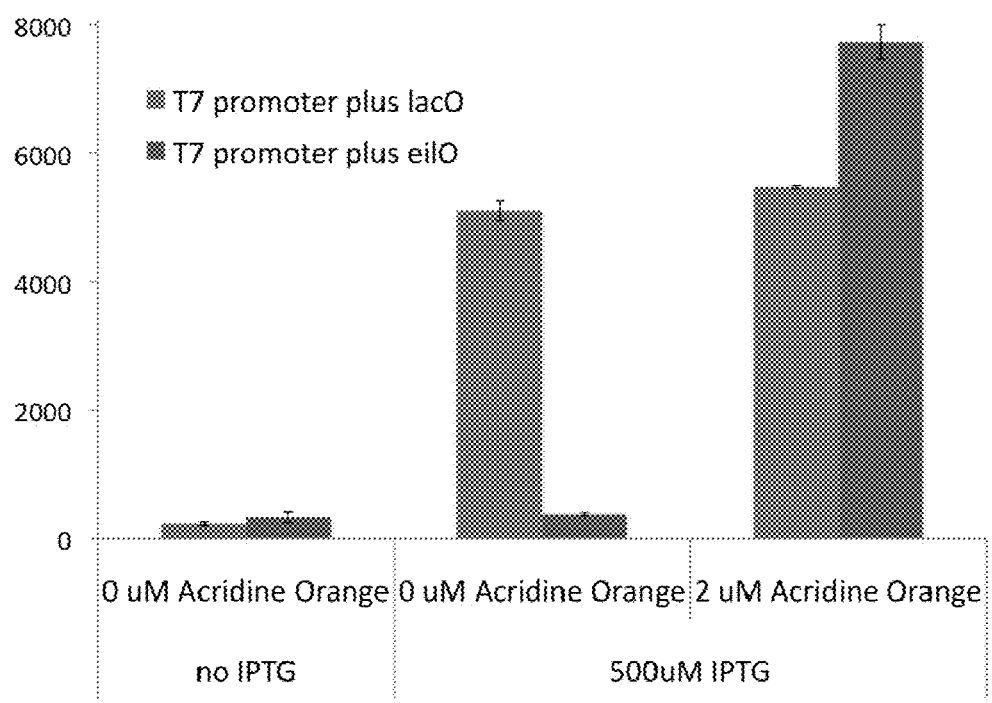
FIG. 9 shows an EilR-regulated T7 phage promoter enables expression rates higher than the common Lac system. RFP was expressed from a T7 promoter controlled either by an IPTG-inducible lac operator or an acridine orange-inducible eil operator. The chromosomal T7-RNA polymerase was expressed from a Lac-promoter in both cases (in E. coli BL21-DE3). In the future, T7 RNA-polymerase expression could also be controlled by an Eil-promoter.
Figure 10:
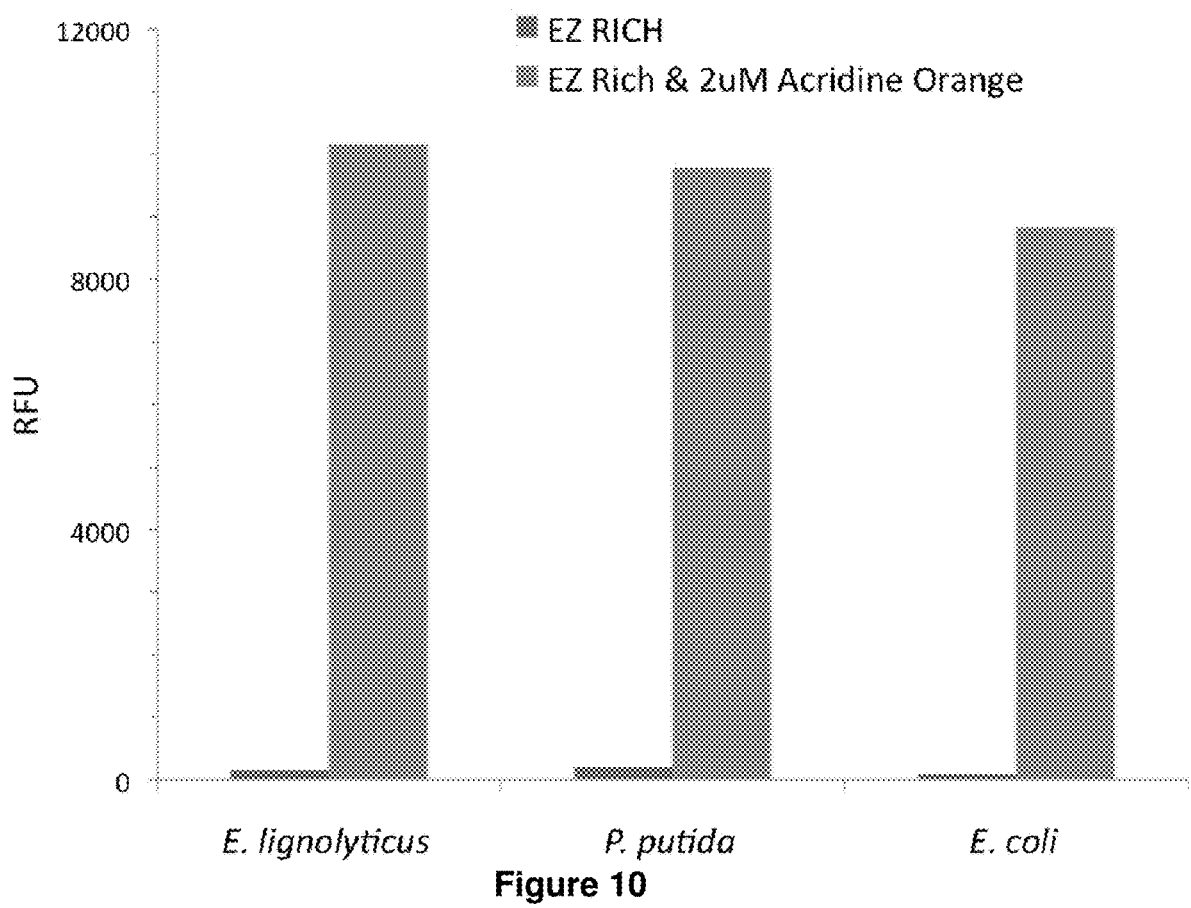
FIG. 10 shows Eil-promoters are functional in various bacteria. Three different gram-negative bacteria express RFP from the p1-promoter (see FIG. 3) when induced by acridine orange. All strains contain the same plasmid (BBR origin of replication).

The functionality of Eil-promoters is not restricted to *E. coli* and offers an expression platform in various host organisms. This is demonstrated in *Enterobacter lignolyticus* and *Pseudomonas putida*. In addition to bacterial promoters, the eil operators can be used to control expression from phage promoters such as T7. FIG. 9 shows an EilR-regulated T7 phage promoter enables expression rates higher than the common Lac system. RFP was expressed from a T7 promoter controlled either by an IPTG-inducible lac operator or an acridine orange-inducible eil operator. The chromosomal T7-RNA polymerase was expressed from a Lac-promoter in both cases (in *E. coli* BL21-DE3). In the future, T7 RNA-polymerase expression could also be controlled by an Eil-promoter. FIG. 10 shows Eil-promoters are functional in various bacteria. Three different gram-negative bacteria express RFP from the p1-promoter (see FIG. 3) when induced by acridine orange. All strains contain the same plasmid (BBR origin of replication).

Figure 11A:
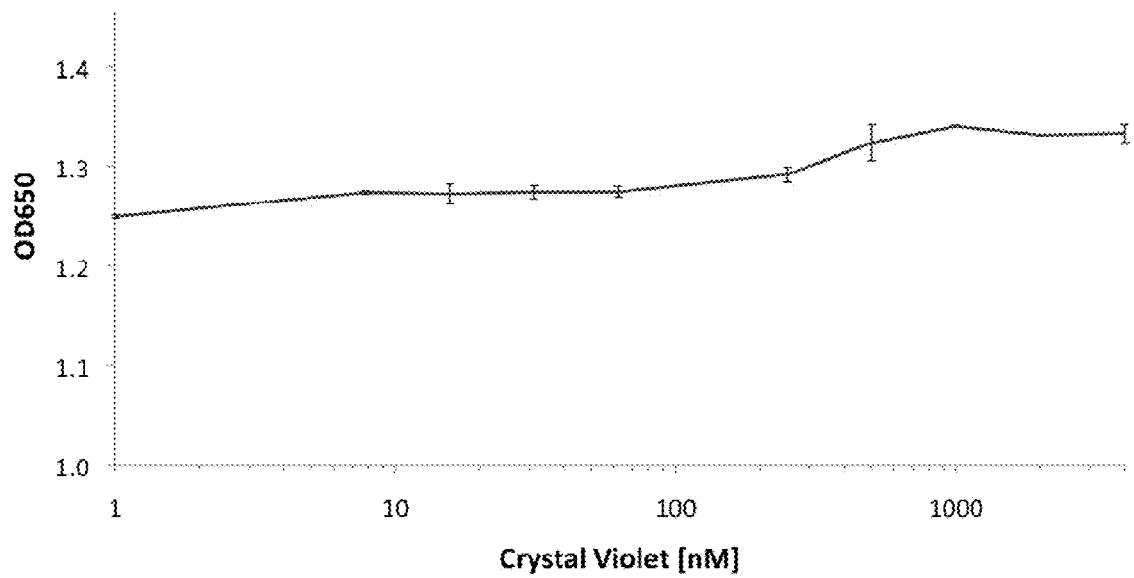
FIG. 11A shows growth of E. coli in the presence of inducer molecules. Cell densities of stationary phase E. coli DH10B grown in EZ-Rich/glucose medium supplemented with crystal violet at concentrations typically used for inducing Eil-promoters.
Figure 11B:
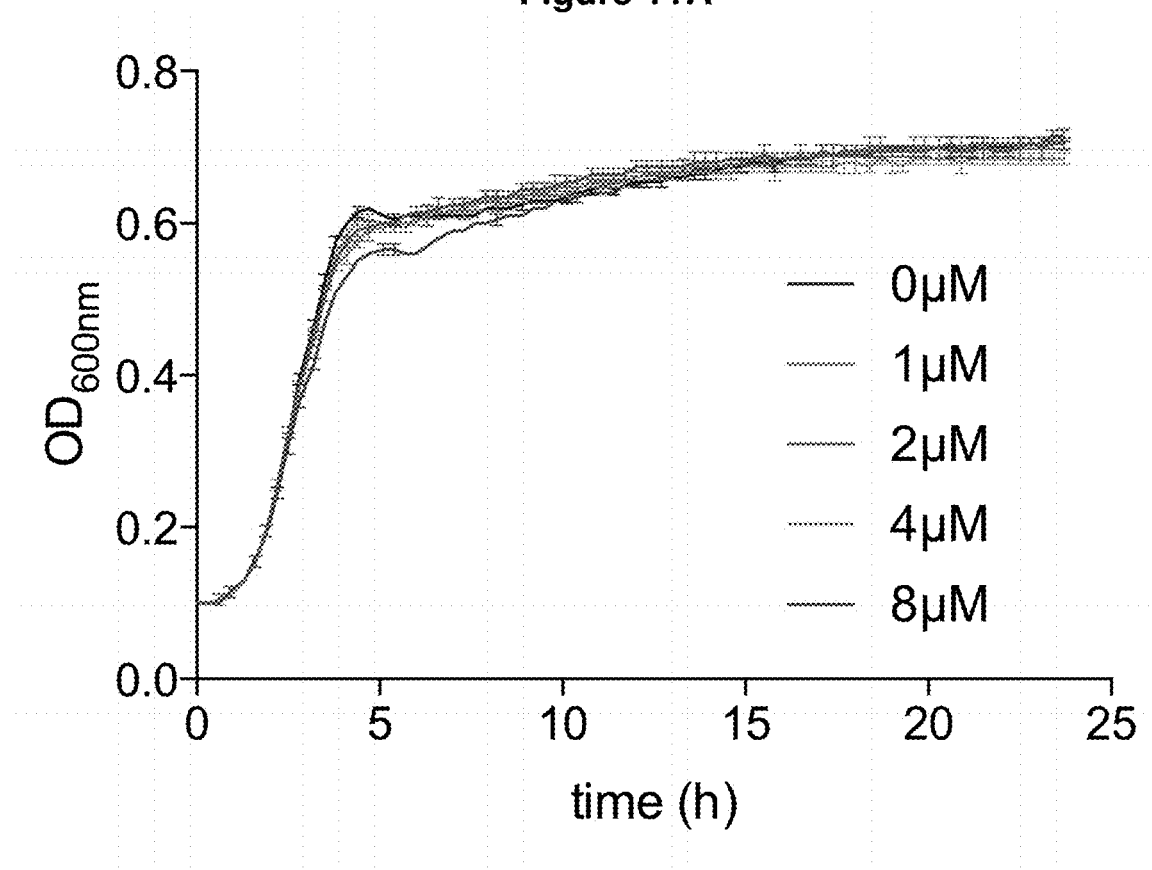
FIG. 11B shows growth of E. coli in the presence of inducer molecules. Growth of E. coli DH10B grown in EZ-Rich/glucose medium supplemented with acridine orange at concentrations typically used for inducing Eil-promoters.

FIGS. 11A and 11B shows growth of *E. coli* in the presence of inducer molecules. FIG. 11A shows cell densities of stationary phase *E. coli* DH10B grown in EZ-Rich/glucose medium supplemented with crystal violet at concentrations typically used for inducing Eil-promoters. FIG. 11B shows the growth of *E. coli* DH10B grown in EZ-Rich/glucose medium supplemented with acridine orange at concentrations typically used for inducing Eil-promoters.

Figure 12:
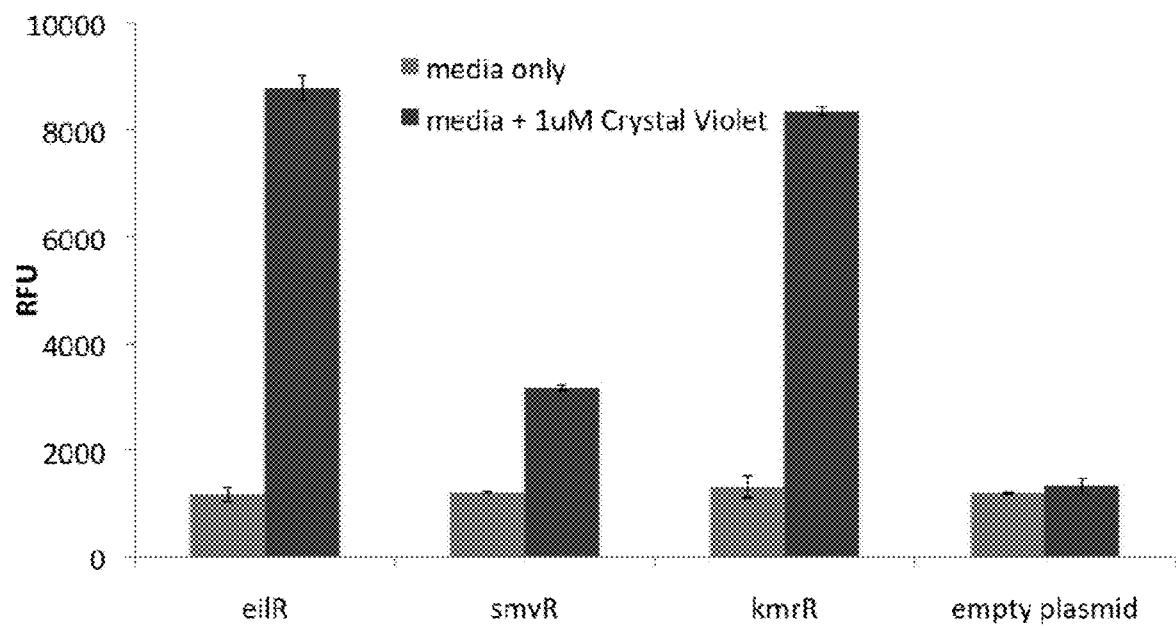
FIG. 12 shows crystal violet induces homologous repressors. The EilR homologues SmvR (from Salmonella typhimurium) and KmrR (from Klebsiella BRL6-2) regulate RFP expression from an Eil-promoter in E. coli. Like EilR, these repressors bind to the eilO consensus operator and are induced e.g. by crystal violet.

FIG. 12 shows crystal violet induces homologous repressors. The EilR homologues SmvR (from *Salmonella typhimurium*) and KmrR (from *Klebsiella* BRL6-2) regulate RFP expression from an Eil-promoter in *E. coli*. Like EilR, these repressors bind to the eilO consensus operator and are induced e.g. by crystal violet.

Figure 13:
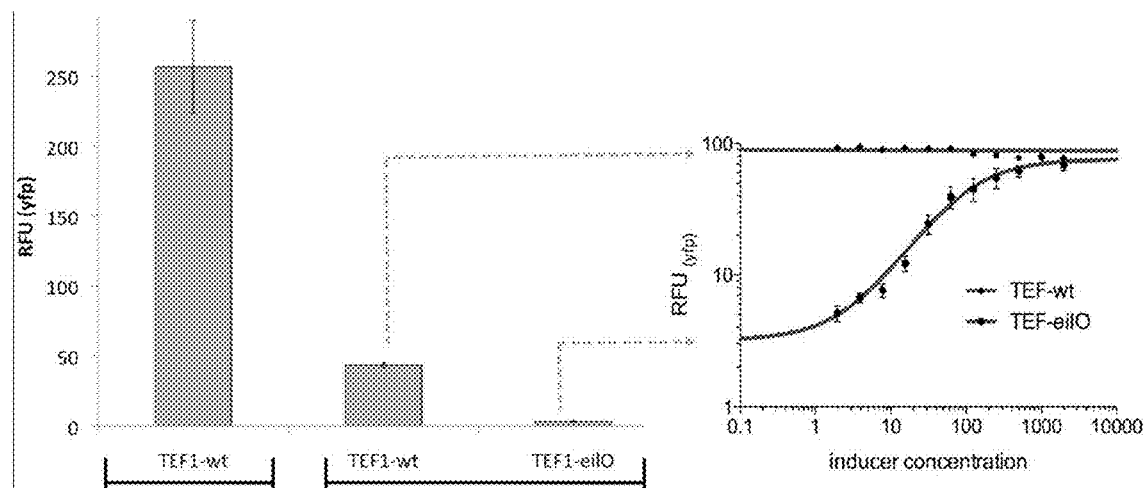
FIG. 13 shows the induction of a TEF-eilO system with the addition of an inducer.

FIG. 13 shows the induction of a TEF-eilO system with the addition of an inducer.

Figure 17:
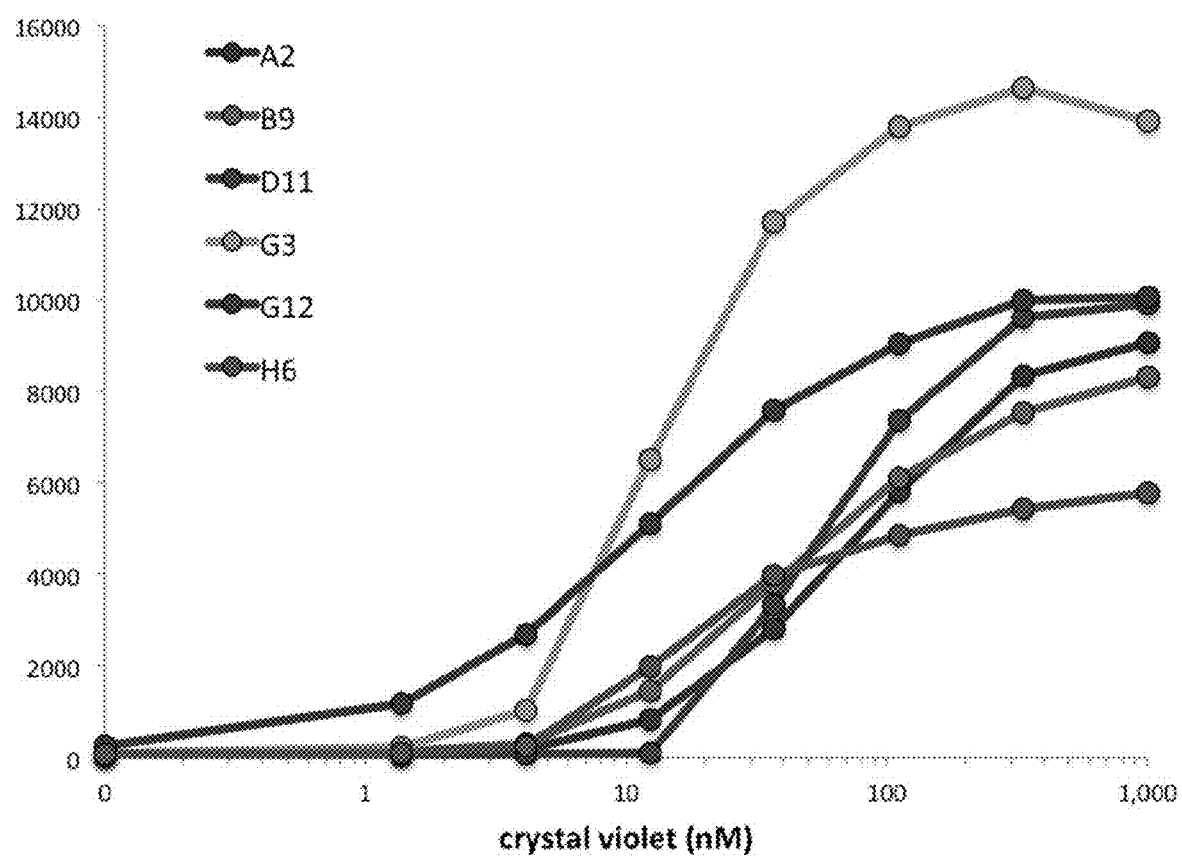
FIG. 17 shows the behavior of EilR-regulated promoter variants in Pseudomonas putida.

FIG. 17 shows the versatility of expression system of the present invention as demonstrated in *Pseudomonas putida*. These examples show engineered promoters with different properties (different inducer concentrations for induction, different dose-response, and different maximum activity when fully induced).

Figure 18A:
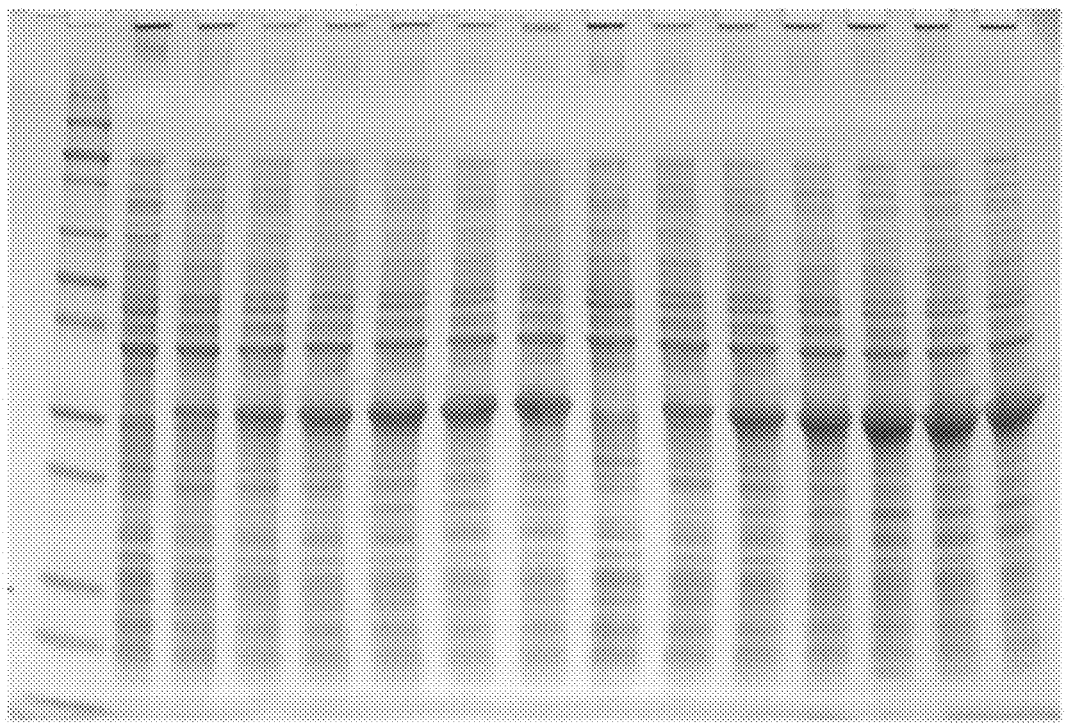
FIG. 18A shows the induction of RFP from a T7 expression system by IPTG.
Figure 18B:
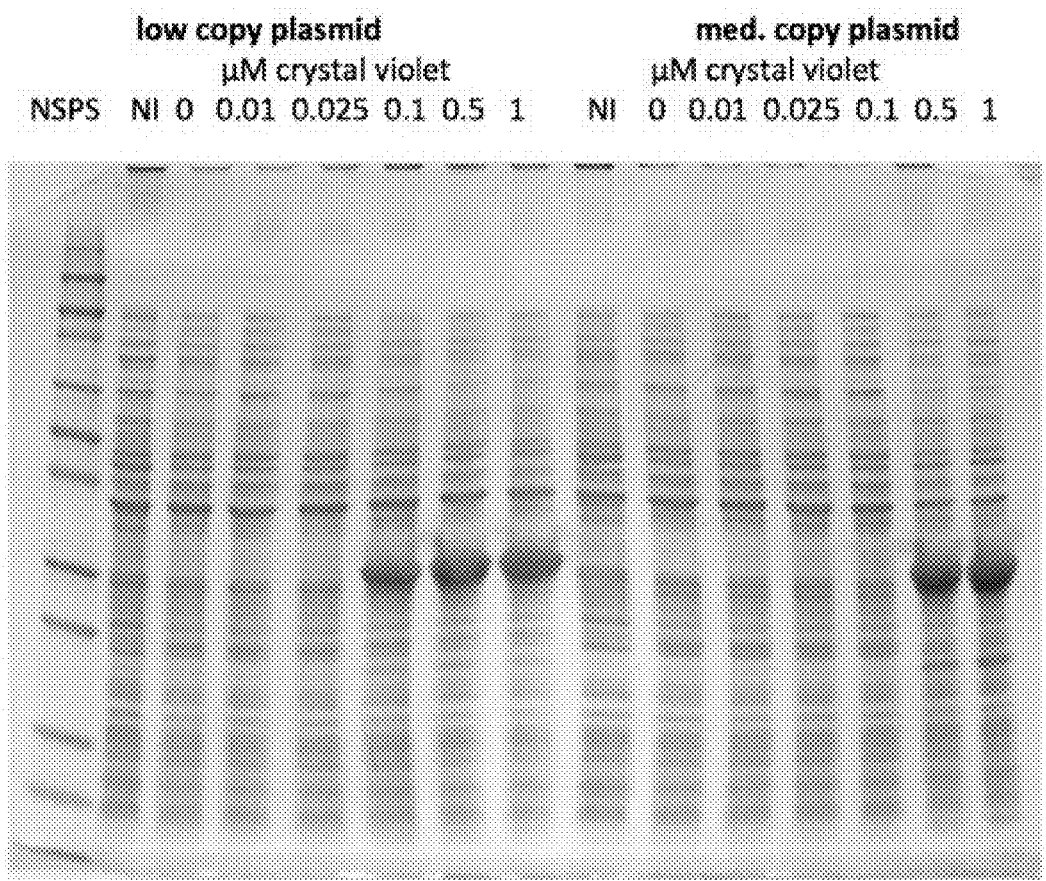
FIG. 18B shows the induction of RFP from an Eil expression system of the present invention by crystal violet.

FIGS. 18A and 18B show SDS page gel of RFP expressed in the T7 system and the system of the present invention, which demonstrates the system of the present invention is capable of higher expression using much less of an inducer molecule.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell comprising
   (a) a first nucleic acid comprising a nucleotide sequence of interest operatively linked to a promoter which is modified to comprise an EilR binding site;
   (b) a second nucleic acid comprising a nucleotide sequence encoding a repressor polypeptide comprising an amino acid sequence comprising a biologically active fragment of EilR having at least 70% amino acid identity with SEQ ID NO:1, wherein expression of the nucleotide sequence of interest from the promoter is induced by the presence of a hydrophobic inducer in that when the repressor polypeptide is bound to the hydrophobic inducer, the repressor polypeptide does not bind to the EilR binding site, and wherein the nucleotide sequence of interest is heterologous to EilR, and wherein the repressor polypeptide is heterologous to the genetically modified host cell, and when the repressor polypeptide has an amino acid sequence consisting of SEQ ID NO:1, then the nucleotide sequence of interest does not encode a green fluorescence protein (GFP);
   (c) the hydrophobic inducer within the genetically modified host cell.

2. The genetically modified host cell of claim 1, wherein the hydrophobic inducer is a hydrophobic cation inducer.

3. The genetically modified host cell of claim 2, wherein the hydrophobic cation inducer is a triarylmethane, acridine, phenazine, phenothiazine, or xanthene.

4. The genetically modified host cell of claim 1, wherein the hydrophobic inducer is a hydrophobic anion inducer.

5. A method for expressing a nucleotide sequence of interest comprising providing the genetically modified host cell of claim 1, and culturing or growing the genetically modified host cell such that the nucleotide sequence of interest is expressed at a rate higher when the hydrophobic cation inducer is present than if the hydrophobic cation inducer is not present in the genetically modified host cell.

6. The genetically modified host cell of claim 1, wherein nucleotide sequence of interest encodes a polypeptide of interest.

7. The genetically modified host cell of claim 1, wherein the genetically modified host cell is a yeast.

8. The genetically modified host cell of claim 7, wherein the yeast is a *Yarrowia, Candida, Bebaromyces, Saccharomyces, Schizosaccharomyces* and *Pichia* cell.

9. The genetically modified host cell of claim 1, wherein the genetically modified host cell is an *Escherichia, Bacillus, Salmonella, Klebsiella, Enterobacter, Pseudomonas, Streptomyces, Cynechocystis, Cynechococcus, Sinorhizobium*, and *Caulobacter* cell.

10. The genetically modified host cell of claim 1, wherein the genetically modified host cell is *Escherichia coli* and the promoter is a lac promoter, trc promoter, tac promoter, T7 promoter, $P_L$ promoter, tetA promoter, araBAD promoter, rhaP$_{BAD}$ promoter, Lambda promoter, or T5 promoter.

11. The method of claim 5, wherein the hydrophobic inducer is a hydrophobic cation inducer.

12. The method of claim 11, wherein the hydrophobic cation inducer is a triarylmethane, acridine, phenazine, phenothiazine, or xanthene.

13. The method of claim 5, wherein the hydrophobic inducer is a hydrophobic anion inducer.

14. The method of claim 5, wherein nucleotide sequence of interest encodes a polypeptide of interest.

15. The method of claim 5, wherein the genetically modified host cell is a yeast.

16. The method of claim 15, wherein the yeast is a *Yarrowia, Candida, Bebaromyces, Saccharomyces, Schizosaccharomyces* and *Pichia* cell.

17. The method of claim 5, wherein the genetically modified host cell is an *Escherichia, Bacillus, Salmonella, Klebsiella, Enterobacter, Pseudomonas, Streptomyces, Cynechocystis, Cynechococcus, Sinorhizobium*, and *Caulobacter* cell.

18. The method of claim 17, wherein the genetically modified host cell is *Escherichia coli* and the promoter is a lac promoter, trc promoter, tac promoter, T7 promoter, $P_L$ promoter, tetA promoter, araBAD promoter, rhaP$_{BAD}$ promoter, Lambda promoter, or T5 promoter.

\* \* \* \* \*